United States Patent [19]

Mitchell

[11] Patent Number: 4,588,717

[45] Date of Patent: May 13, 1986

[54] COMPOUNDS AND VITAMIN SUPPLEMENTS AND METHODS FOR MAKING SAME

[75] Inventor: David C. Mitchell, Salt Lake City, Utah

[73] Assignee: David C. Mitchell Medical Research Institute, Salt Lake City, Utah

[21] Appl. No.: 620,131

[22] Filed: Jun. 13, 1984

[51] Int. Cl.$^4$ ................... A01N 45/00; A61K 31/56
[52] U.S. Cl. ................... 514/170; 514/171; 514/182; 260/397.1; 260/397.2; 260/397.5; 556/46; 556/58; 556/88; 556/112; 556/122; 556/140; 558/82
[58] Field of Search ............. 260/397.2, 397.5, 429; 514/170, 171

[56] References Cited

U.S. PATENT DOCUMENTS 4,309,448  1/1982  Takaishi et al. ............. 260/397.2
4,444,884  4/1984  Sih ............................ 435/55

FOREIGN PATENT DOCUMENTS 775835  5/1957  United Kingdom ............. 260/397.2

OTHER PUBLICATIONS

John W. Frost, "5-Thio-D-Glucose: How Do Enzymes Work?", 16 Aldrichimica Acta 39, No. 2 (1983), a publication of Aldrich Chemical Company, Milwaukee, Wisconsin.

*Primary Examiner*—Elbert L. Roberts
*Attorney, Agent, or Firm*—Workman, Nydegger & Jensen

[57] ABSTRACT

The present invention relates to novel compounds, vitamin supplements, diet pills, and methods for making the same. The vitamin supplements include one or more phytosterol esters, such as esters of sitosterol or stigmasterol, and/or one or more novel substituted fructose compounds. The diet pills within the scope of the invention include antitrypsin, and may be combined with the vitamin supplements to provide diet vitamin supplements.

40 Claims, No Drawings

COMPOUNDS AND VITAMIN SUPPLEMENTS AND METHODS FOR MAKING SAME

BACKGROUND

1. Field of the Invention

The present invention relates to novel compounds and vitamin supplements and methods for making the same. In particular, the present invention relates to the manufacture and use of phytosterol esters, novel substituted fructose compounds, and antitrypsin enzyme in vitamin supplements.

2. The Prior Art

A. Steriod Vitamin Supplements

It is well known that steriods and hormones promote healing of the human body, maintain the integrity of the body cells, support brain functions, and promote the reproductive processes. The cells of both plants and animals exert large amounts of energy in making the necessary steriods and hormones for their daily functions. It has been generally recognized that, if steriod levels in the body cells of a human being could be raised to pre-puberty levels, much less strain would be placed upon the cells, thus resulting in healthier cells which experience a greater longevity.

Hence, attempts have been made in the prior art to provide vitamin supplements which supply steroids and hormones to the human body. For example, many vitamin supplements incorporate Vitamin A for this purpose. Vitamin A itself is a precursor for steroids, and can be converted by the human body into steroids.

However, vitamin supplements containing Vitamin A suffer from the drawback that a relatively large amount of energy must still be exerted by the body cells to convert the Vitamin A into steroids, thus resulting in a significant amount of stress to the cells. Moreover, it is well known that high dosage levels of Vitamin A can be toxic to the body cells.

Other attempts have been made to introduce steroids and hormones directly into the human body, either by oral consumption or by injection. However, direct introduction of steroids and hormones into the digestive tract and/or blood stream of an individual can result in various undesirable side effects.

Some of the undesirable side effects encountered as a result of the direct administration of steroids and hormones into the human body include androgenic effects, acne, voice changes, menstrual irregularities, post-menopausal bleeding, swelling of the breasts, nausea, edema, hypersensitivity, hypermetabolism, hypercalcemia, flushing, and congestive heart failure. Additionally, steroid and hormone injections have also been linked to osteoporosis.

Besides the undesirable side effects associated with steroids and hormones, there is a poor absorption of orally ingested steroids and hormones into the human digestive tract. Additionally, many steroids and hormones are converted into toxic substances in the digestive tract.

Hence, it will be appreciated that what is needed in the art is a chemical formulation and method for administering steroids and hormones to humans and other animals without directly introducing the hormones and steroids into the blood stream or digestive tract. It would be a further significant advancement in the art to provide a chemical formulation and method of supplying steroids and hormones to the cells of both animals and plants wherein undesirable side effects of the steroids and hormones are substantially avoided. Further, it would be another advancement in the art to provide chemical formulations and methods for supplying steroids and hormones to the cells of both animals and plants wherein the energy exerted by the cells is minimized and the stress experienced by the cells is minimized. Such chemical formulations and methods are disclosed and claimed herein.

B. Mineral Vitamin Supplements

It is well known that there are various minerals which have nutritional value to plants and animals. Many different vitamin supplements have been prepared in the prior art in order to achieve effective absorption of these minerals into, for example, the human body.

For example, amino acid salts of minerals (e.g., monosodium glutamate) and protein salts of minerals have been used to introduce various minerals into the human body. Unfortunately, these mineral salts dissociate quickly upon entering the digestive tract or blood stream of the individual, thus releasing the minerals as ions into the digestive tract and blood stream. These mineral ions are often toxic when located in areas outside of the body cells, and thus such sudden release of the mineral ions into the digestive tract and blood stream can be detrimental to the individual. Additionally, the absorption of the amino acid mineral salts and protein mineral salts into the human body is limited.

Fumaric acid salts and gluconic acid salts of minerals (sometimes referred to as fumarates and gluconates, respectively) have also been used as mineral vitamin supplements. As with the amino acid mineral salts and protein mineral salts, fumaric and gluconic acid mineral salts have exhibited unacceptable levels of toxicity. Moreover, the absorption of these mineral salts into the human body is also limited.

Thus, it will be appreciated that what is needed in the art is a mineral vitamin supplement wherein the minerals are not released in toxic form into the digestive tract and blood stream before reaching the body cells of the animal. It would be another significant advancement in the art to provide mineral vitamin supplements and methods for achieving more effective absorption of minerals into both animals and plants. Such mineral vitamin supplements and methods are disclosed and claimed herein.

C. Diet Pills and Preparations

Many different prior art diet pills and preparations have been formulated in an attempt to help individuals lose weight. Most diet pills and preparations include some sort of stimulant, typically a member of the amphetamine family, in order to increase the basal metabolic rate of the individual. For example, compounds such as prolamine, methylamphetamine, norepinephrine, and pseudo epinephrine have been used in diet pills.

Unfortunately, the prior art diet pills and preparations suffer from several drawbacks. First of all, many of the amphetamine stimulants used in these pills and preparations are addictive and thus cause the users to become dependent upon them. These stimulants also serve to speed up the metabolism of the individual, causing such adverse effects as anxiety, irritability, and insomnia. Further, as the effects of the stimulants wear off, it is common for the user to experience periods of depression, and many individuals tend to ingest large amounts of food when depressed. Moreover, the prior art diet pills and preparations attempt to reduce the individual's desire for caloric intake, and this often results in a self-deprivation of the nutritional substances which are vital to the proper functioning of the body.

From the foregoing, it will be appreciated that what is needed in the art is a diet pill and method of aiding an individual to lose weight wherein the adverse side effects of the prior art diet pills, e.g., addiction and depression, are substantially avoided. It would be a further advancement in the art to provide a diet pill which would allow an individual to lose weight while maintaining normal caloric intake and thereby ensure consumption of the necessary nutritional substances needed for proper operation and maintenance of the individual's body. Such diet pills and methods are disclosed and claimed herein.

BRIEF SUMMARY AND OBJECTS OF THE INVENTION

The present invention relates to the use of phytosterol esters, novel substituted fructose compounds, and antitrypsin enzyme in vitamin supplements and to the manufacture of such vitamin supplements.

In one vitamin supplement of the present invention, phytosterol esters such as fatty acid esters of sitosterol, stigmasterol, and taraxasterol, in various combinations, are preferably mixed with a pharmaceutically acceptable carrier material so as to form a vitamin supplement. The fatty acids used to form the phytosterol esters have from about 18 to about 20 carbon atoms and at least two carbon-to-carbon double bonds. In some presently preferred embodiments, fatty acids such as linoleic acid, linolenic acid, and arachidonic acid are used to form the phytosterol esters.

In the phytosterol ester vitamin supplements of the present invention, steroids and hormones are produced after the vitamin supplements reach the cells of the animal or plant. Hence, the phytosterol ester vitamin supplements of the present invention are introduced into the animal or plant as relatively non-toxic phytosterol esters which are then converted to steroids and hormones only after reaching the cells, thereby minimizing the adverse side-effects of steroids and hormones experienced in the prior art when the steroids and hormones are introduced directly into the digestive tract and bloodstream. Further, the phytosterol ester vitamin supplements of the present invention are readily converted by the cells of the animal or plant to steroids and hormones with a minimal amount of energy exertion by the cells, thereby minimizing the stress placed on the cells and extending their longevity. Finally, the phytosterol ester vitamin supplements of the present invention provide a unique and efficient manner of achieving absorption of phytosterols into the cells of the animal or plant, with the fatty acid portion of the ester serving to significantly enhance such absorption.

Another vitamin supplement of the present invention involves the incorporation of one or more novel substituted fructose compounds into a pharmaceutically acceptable carrier material to form a vitamin supplement. In each of the novel substituted fructose compounds used in these vitamin supplements, a mineral having nutritional value, e.g., calcium, cobalt, chromium, copper, iron, magnesium, manganese, molybdenum, nickel, phosphorous, selenium, tin, vanadium, or zinc, is incorporated into the fructose ring structure. This is accomplished by substituting a single atom of the mineral for the number six carbon in the fructose ring structure.

When such a mineral vitamin supplement is administered to an animal, the mineral is not released from the substituted fructose ring structure until reaching the cells of the animal, thereby avoiding the toxic release of mineral ions into the digestive tract and blood stream as experienced in the prior art mineral vitamin supplements. Moreover, the substituted fructose ring structure carrying the mineral in the mineral vitamin supplements of the present invention is readily absorbed by both animals and plants, thereby increasing absorption and delivery of the minerals to the cells of the animals and plants.

The present invention also contemplates a diet pill or diet vitamin supplement. In the diet pill of the present invention, antitrypsin enzyme is placed in a pharmaceutically acceptable enzyme stabilizing material to serve as the diet pill. Additionally, amylase inhibitor may be added to the diet pill if desired.

The diet pills of the present invention are not characterized by the adverse side-effects, such as addiction and depression, which are experienced with the use of the prior art diet pills. Further, the diet pills of the present invention serve to reduce the absorption of carbohydrates ingested by an individual into the body so that a portion of the carbohydrates ingested by the individual are passed through normal excretory channels. Hence, the diet pills of the present invention provide a means for allowing an individual to lose weight while maintaining normal caloric intake and at the same time ensuring consumption of the necessary nutritional substances needed for the proper maintenance of the body of the individual. Finally, because the diet pills of the present invention reduce the absorption of carbohydrates by the body rather than speeding up the metabolism of the body to burn carbohydrates as is the case with many prior art diet pills, use of the diet pills of the present invention does not cause anxiety, irritability, or insomnia.

The present invention also contemplates various combinations of the foregoing steroid vitamin supplements, mineral vitamin supplements which may be used, and diet pills into various vitamin supplements which may be used for different purposes. Additionally, virtually any ingredients used in prior art vitamin supplements may be combined with the various combinations of the foregoing components used in the vitamin supplements of the present invention.

It is, therefore, an object of the present invention to provide novel vitamin supplements and methods for supplying steroids and hormones to the cells of both animals and plants.

Another object of the present invention is to provide novel substituted fructose compounds and methods for producing such compounds.

Still another object of the present invention is to provide novel vitamin supplements and methods for supplying minerals to the cells of both animals and plants.

Yet another object of the present invention is to provide vitamin supplements and methods for supplying steroids and minerals directly to the cells of both animals and plants which vitamin supplements are not toxic to the animals and plants and are readily absorbed by the animals and plants.

A further object of the present invention is to provide steroid vitamin supplements wherein steroids and hormones are produced with a minimal amount of energy exerted by the cells of the animals and plants and wherein the adverse side-effects exhibited by the prior art steroid vitamin supplements are minimized, if not substantially eliminated.

Another object of the present invention is to provide a novel diet pill for aiding individuals to lose weight.

Still another object of the present invention is to provide diet pills and diet vitamin supplements which avoid the adverse side-effects of the prior art diet pills and which allow individuals to lose weight while maintaining normal caloric intake and thereby ensure consumption of the necessary nutritional substances needed for proper maintenance of the body.

These and other objects and features of the present invention will become more fully apparent from the following description and appended claims.

DETAILED DESCRIPTION OF THE PREFERRED EMBODIMENTS

A. The Steroid Vitamin Supplements of the Present Invention

The steroid vitamin supplements of the present invention comprise one or more phytosterol esters, preferably in a pharmaceutically acceptable carrier material. As used herein, the term "phytosterol" includes all phytosterols, for example, sitosterol, stigmasterol, taraxasterol, and any derivatives of the foregoing. Hence, it will be appreciated that modifications of phytosterol compounds to include, for example, small side chains, are also well within the scope of the present invention.

Many different pharmaceutically acceptable carrier materials are well-known in the art and may be used for purposes of the steroid vitamin supplements of the present invention. For example, such carrier materials as cellulose acetate, phenyl salicylate, corn starch, and fructose may be used as carrier materials. However, it will be appreciated that these carrier materials are given by way of example only, and that there are many other pharmaceutically acceptable carrier materials which may be use in accordance with the present invention.

Preferably, each steroid vitamin supplement of the present invention includes an ester of sitosterol or an ester of stigmasterol or both. It is the sitosterol ester and the stigmasterol ester which provide the steroids and hormones in the steroid vitamin supplements of the present invention. To the sitosterol ester and/or stigmasterol ester may be added a taraxasterol ester which serves to enhance absorption of the sitosterol ester and/or stigmasterol ester into the animal or plant host. In one presently preferred embodiment of the present invention, the steroid vitamin supplement contains a sitosterol ester, a stigmasterol ester, and a taraxasterol ester.

To form the phytosterol esters used in the steroid vitamin supplements of the present invention, fatty acids are condensed with the phytosterols. These fatty acids have from about 18 to about 20 carbon atoms in the main carbon chain and at least two carbon-to-carbon double bonds. The most presently preferable fatty acid which has been found acceptable for purposes of the present invention is linoleic acid. This is primarily because linoleic acid is both inexpensive and stable. Other fatty acids which have been found acceptable for purposes of the present invention include linolenic acid and arachidonic acid.

It will, however, be appreciated that derivatives of linoleic acid, linolenic acid, and arachidonic acid, such as the addition of small side chains, are also within the scope of the present invention. Further, it should be understood that virtually any fatty acid having from about 18 to about 20 carbon atoms in the main carbon chain and at least two carbon-to-carbon double bonds, in addition to terminal carboxyl and methyl groups, may be used for purposes of the present invention, and many fatty acids are included within this category. Although fatty acids having less than 18 carbon atoms in the main carbon chain or more than 20 carbon atoms in the main carbon chain may be used, it has been found that phytosterol esters made from such fatty acids tend to have less utility in achieving the purposes of the present invention.

The phytosterols which are used to form the phytosterol esters in the steroid vitamin supplements of the present invention may be procured from a variety of natural sources. For example, sitosterol may be obtained from cold pressed wheat germ oil, soy extract, or rice extract. (It will be appreciated that natural sitosterol contains about 40% alpha-sitosterol and about 60% beta-sitosterol. Both the alpha and beta forms of sitosterol may be used to form sitosterol esters in the steroid vitamin supplements of the present invention.) Stigmasterol is also found in trace amounts in cold pressed wheat germ oil, soy extract, and rice extract. Taraxasterol may be obtained from licorice root extract and dandelions.

Taraxasterol is a member of the picane steroid family. Although taraxasterol is presently the most preferred picane steroid which may be used in accordance with the present invention, it will be understood that other picane steroids may also be used in accordance with the present invention. For example, members of the picane steroid family such as beta-glycyrhetinic acid, oleanolic acid, and taraxerol may also be used with the present invention.

Below are the formulas for alpha-sitosterol, beta-sitosterol, stigmasterol, and taraxasterol:

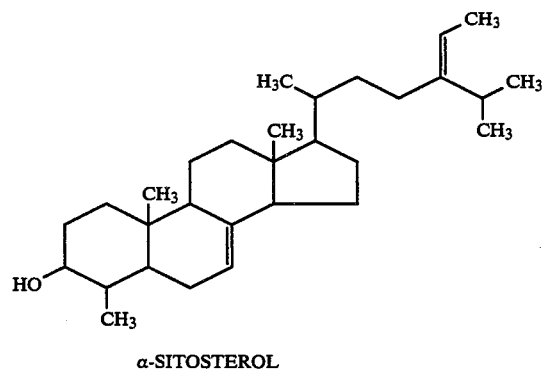

α-SITOSTEROL

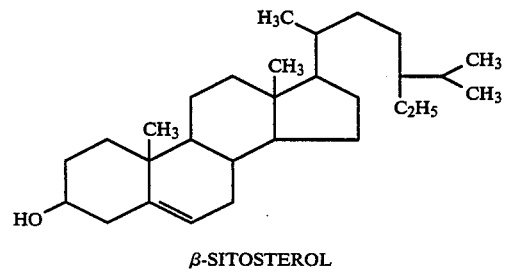

β-SITOSTEROL

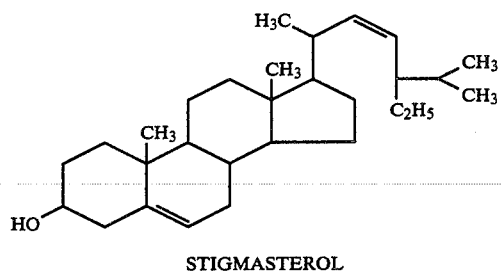

STIGMASTEROL

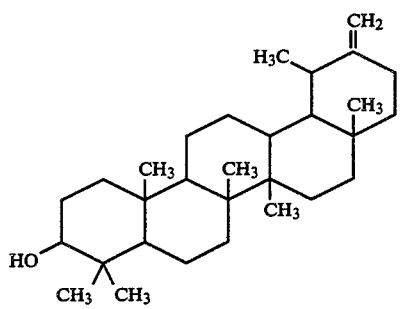

TARAXASTEROL

Many of the fatty acids used in the present invention may also be obtained from natural sources. For example, linoleic acid may be obtained from safflower oil, olive oil, and corn oil. Linolenic acid and arachidonic acid are found in safflower oil, olive oil, and jojoba oil.

Below are the formulas for linoleic acid, linolenic acid, and arachidonic acid:

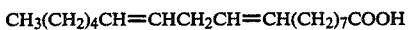

LINOLEIC ACID

LINOLENIC ACID

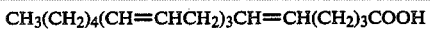

ARACHIDONIC ACID

Normally, sitosterol, stigmasterol, taraxasterol, and any other phytosterols are not absorbed by animals and plants to an appreciable extent in their natural state. However, the inventor of the present invention has found that by condensing the hydroxyl group of each of these phytosterols with the carboxyl group of a fatty acid selected from the group discussed herein to form an ester, surprising absorption of the resultant phytosterol esters into both animal and plant hosts alike is achieved.

To form a phytosterol ester in accordance with the present invention, a selected phytosterol and fatty acid are mixed together and allowed to react under conditions which will permit condensation of the phytosterol with the fatty acid to form an ester. For example, by mixing the phytosterol and fatty acid, bringing the mixture to a temperature of from about 15° C. to about 45° C. at about atmospheric pressure for about one to about three hours a phytosterol ester will be produced in accordance with the present invention.

The reaction between any given phytosterol and any given fatty acid is essentially the same, and is characterized in Equation 1 below using sitosterol as an exemplary phytosterol and linoleic acid as an exemplary fatty acid:

EQUATION I

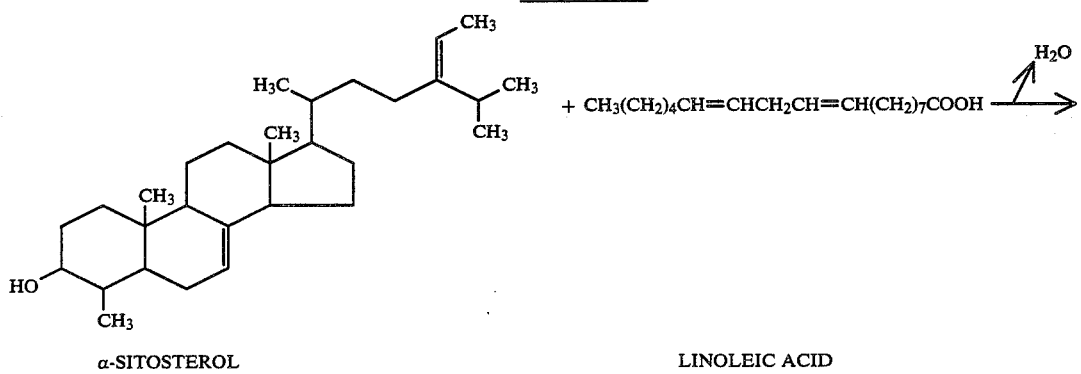

α-SITOSTEROL           LINOLEIC ACID

-continued
EQUATION I

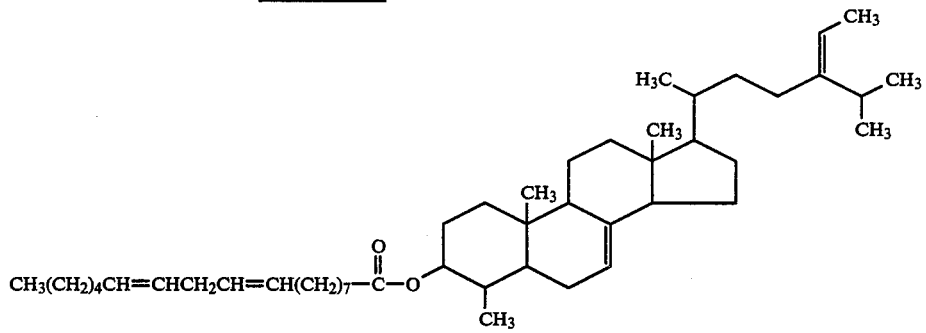

$$CH_3(CH_2)_4CH=CHCH_2CH=CH(CH_2)_7-\overset{O}{\underset{\|}{C}}-O$$

LINOLEIC ACID ESTER OF α-SITOSTEROL

Again, it will be appreciated that Equation 1 above relates to the formation of all phytosterol esters in accordance with the present invention, regardless of the particular phytosterol and fatty acid employed.

For purposes of the steroid vitamin supplements of the present invention, it has been found that inclusion of enough sitosterol ester, stigmasterol ester, and taraxasterol ester in the vitamin supplement to provide a daily dosage of up to about 10 milligrams of sitosterol, up to about 10 milligrams of stigmasterol. and up to about 2 milligrams of taraxasterol, per kilogram of animal body weight. produces the desirable effects of the present invention. In plant hosts, inclusion of sufficient sitosterol ester, stigmasterol ester, and taraxasterol ester to provide a monthly dosage of up to about 20 milligrams of sitosterol, up to about 20 milligrams of stigmasterol, and up to about 5 milligrams of taraxasterol per foot of height of the plant is typically sufficient to produce the desirable results of the present invention.

However, it will of course be recognized that daily dosages larger than this may be administered to an animal or plant host, and that the exact daily dosage will depend upon the nature, size, and specific characteristics of the host treated. It will also be recognized that the inclusion of much larger amounts of the various phytosterol esters, although not harmful to the animal or plant host, will only result in dosages which cannot fully be utilized by the animal or plant host, and the excess amount of these phytosterol esters not used by the host will pass through normal excretory channels.

The phytosterol ester vitamin supplements of the invention may be administered orally, topically, or parenterally to an animal host, while topical administration is generally preferred for plant hosts. Exemplary phytosterol ester vitamin supplements within the scope of the present invention which may be employed in these various modes of application are given below.

EXAMPLE 1

In this example, a phytosterol ester vitamin supplement in the form of a pill was prepared in accordance with the present invention for oral administration to animals. The vitamin pill of this example was prepared at room temperature (about 20° C.) and pressure. (The generally preferred temperature range for making the phytosterol vitamin supplements of the present invention is from about 15° C. to about 45° C.) Under these conditions, about 720 milligrams of safflower oil (about 76% linoleic acid) were blended together with about 50 milligrams of ascorbic acid acting as an antioxidant and about 20 milligrams of calcium propionate acting as a preservative. Subsequently, about 1 gram of petrolatum (medium, $C_{20}$–$C_{40}$) were added to the mixture and thoroughly blended therewith. Finally, about 1 gram of sitosterol (comprising a 40% alpha-sitosterol/60% beta-sitosterol blend) was blended into the mixture. This mixture required about 1 hour in order for the sitosterol and linoleic acid to react to form the linoleic acid ester of sitosterol. The resultant product was then added to about 7.2 grams of calcium lactate which served as a filler or carrier material, and 10 vitamin pills were produced in this example by pressing the resultant mixture in a conventional pill press. For the average adult human (i.e., weighing about 70 kilograms), about 3 of these pills should be taken on a daily basis.

In lieu of using a filler material such as calcium lactate, the foregoing blended ingredients could be encapsulated, for example, in hard gelatin capsules so as to form a pill. This alternative encapsulation procedure could also be used for all other examples of the present invention involving a pill.

EXAMPLE 2

In this example, a phytosterol ester vitamin supplement in the form of a pill was prepared in accordance with the present invention for oral administration to animals. The vitamin pill of this example was prepared at room temperature (about 20° C.) and pressure. Under these conditions, about 720 milligrams of safflower oil (about 76% linoleic acid) were blended together with about 30 milligrams of Vitamin E acting as an antioxidant and about 10 milligrams of sodium benzoate acting as a preservative. Subsequently, about 0.9 grams of petroleum jelly ($C_8$–$C_{60}$) were added to the mixture and thoroughly blended therewith. Finally, about 500 milligrams of stigmasterol were blended into the mixture. This mixture required about 1½ hours in order for the stigmasterol and linoleic acid to react to form the linoleic acid ester of stigmasterol. The resultant product was then added to about 7.7 grams of calcium lactate which served as a filler or carrier material, and 10 vitamin pills were produced in this example by pressing the resultant mixture in a conventional pill press. For the average adult human, about 3 of these pills should be taken on a daily basis.

EXAMPLE 3

In this example, a phytosterol ester vitamin supplement in the form of a pill was prepared in accordance with the present invention for oral administration to animals. The vitamin pill of this example was prepared at room temperature (about 20° C.) and pressure. Under these conditions, about 720 miligrams of safflower oil (about 76% linoleic acid) were blended together with about 75 milligrams of butylhydroxy toluene (BHT) acting as an antioxidant and about 25 milligrams of potassium tartrate acting as a preservative. Subsequently, about 0.8 grams of petrolatum ($C_{30}$–$C_{60}$) were added to the mixture and thoroughly blended therewith. Finally, about 750 milligrams of sitosterol (comprising a 37% alpha-sitosterol/63% beta-sitosterol blend) and about 250 milligrams of taraxasterol were blended into the mixture. This mixture required about 2 hours in order for the sitosterol and taraxasterol to react with the linoleic acid to form linoleic acid esters of sitosterol and taraxasterol. The resultant product was then added to about 7.4 grams of calcium lactate which served as a filler or carrier material, and 10 vitamin pills were produced in this example by pressing the resultant mixture in a conventional pill press. For the average adult human, about 3 of these pills should be taken on a daily basis.

EXAMPLE 4

In this example, a phytosterol ester vitamin supplement in the form of a pill was prepared in accordance with the present invention for oral administration to animals. The vitamin pill of this example was prepared at room temperature (about 20° C.) and pressure. Under these conditions, about 720 milligrams of safflower oil (about 76% linoleic acid) were blended together with about 35 milligrams of Vitamin E acting as an antioxidant and about 65 milligrams of calcium propionate acting as a preservative. Subsequently, about 1.1 grams of petrolatum liquid were added to the mixture and thoroughly blended therewith. Finally, about 600 milligrams of stigmasterol and about 50 milligrams of taraxasterol were blended into the mixture. This mixture required about 1 hour in order for the stigmasterol and taraxasterol to react with the linoleic acid to form linoleic acid esters of stigmasterol and taraxasterol. The resultant product was then added to about 7.4 grams of calcium lactate which served as a filler or carrier material, and 10 vitamin pills were produced in this example by pressing the resultant mixture in a conventional pill press. For the average adult human, about 3 of these pills should be taken on a daily basis.

EXAMPLE 5

In this example, a phytosterol ester vitamin supplement in the form of a pill was prepared in accordance with the present invention for oral administration to animals. The vitamin pill of this example was prepared at room temperature (about 20° C.) and pressure. Under these conditions, about 720 milligrams of safflower oil (about 76% linoleic acid) were blended together with about 45 milligrams of Vitamin C acting as an antioxidant and about 15 milligrams of potassium nitrate acting as a preservative. Subsequently, about 0.75 grams of liquid parrafin ($C_5$–$C_{60}$) were added to the mixture and thoroughly blended therewith. Finally, about 500 milligrams of sitosterol (comprising a 34% alpha-sitosterol/66% beta-sitosterol blend) and about 0.5 grams of stigmasterol were blended into the mixture. This mixture required about 2 hours in order for the sitosterol and stigmasterol to react with the linoleic acid to form linoleic acid esters of sitosterol and stigmasterol. The resultant product was then added to about 7.5 grams of calcium lactate which served as a filler or carrier material, and 10 vitamin pills were produced in this example by pressing the resultant mixture in a conventional pill press. For the average adult human, about 3 of these pills should be taken on a daily basis.

EXAMPLE 6

In this example, a phytosterol ester vitamin supplement in the form of a pill was prepared in accordance with the present invention for oral administration to animals. The vitamin pill of this example was prepared at room temperature (about 20° C.) and pressure. Under these conditions, about 720 milligrams of safflower oil (about 76% linoleic acid) were blended together with about 20 milligrams of sodium ascorbate acting as an antioxidant and about 30 milligrams of potassium sorbate acting as a preservative. Subsequently, about 0.85 grams of liquid parrafin ($C_5$–$C_{60}$) were added to the mixture and thoroughly blended therewith. Finally, about 100 milligrams of sitosterol (comprising a 20% alpha-sitosterol/80% beta-sitosterol blend), about 375 milligrams of stigmasterol, and about 100 milligrams of taraxasterol were blended into the mixture. This mixture required about 1 hour in order for the sitosterol, stigmasterol, and taraxasterol to react with the linoleic acid to form linoleic acid esters of sitosterol, stigmasterol, and taraxasterol. The resultant product was then added to about 7.8 grams of calcium lactate which served as a filler or carrier material, and 10 vitamin pills were produced in this example by pressing the resultant mixture in a conventional pill press. For the average adult human, about 3 of these pills should be taken on a daily basis.

EXAMPLES 7–12

In these examples, phytosterol ester vitamin supplements in the form of a cream were prepared in accordance with the present invention for topical administration to animals. The vitamin creams of Examples 7–12 were prepared in identical fashion to the vitamin pills of Examples 1–6, respectively, with the exception that instead of adding the resultant phytosterol esters to calcium lactate as a filler material, the phytosterol esters were added to about 8 grams of palmitic acid which served as a cream base for the topical vitamin creams of each of Examples 7–12. These vitamin creams should be applied to an animal host on a daily basis.

EXAMPLE 13

In this example, a phytosterol ester vitamin supplement in the form of a cream was prepared in accordance with the present invention for topical administration to animals. The vitamin cream of this example was prepared at room temperature and pressure. Under these conditions, about 1.65 grams of corn oil (containing about 1 gram of linoleic acid) were blended together with about 300 milligrams of Vitamin C acting as an antioxidant and about 10 milligrams of calcium propionate as a preservative. Subsequently, about 5 grams of petroleum jelly were added to the mixture and thoroughly blended therewith. Finally, about 500 milligrams of alpha-sitosterol, about 200 milligrams of beta-sitosterol, about 200 milligrams of stigmasterol, and about 160 milligrams of taraxasterol were blended into the mixture. This mixture required about 1½ hours in order for the phytosterols and linoleic acid to react to form linoleic acid esters of the phytosterols. The resultant product was then added to about 100 grams of palmitic acid which served as a cream base for the topical vitamin cream of this example. This vitamin cream should be applied to an animal host on a daily basis.

EXAMPLE 14

In this example, a phytosterol ester vitamin supplement in the form of a powder suitable for spraying or otherwise applying to a plant host was prepared in accordance with the present invention. The vitamin powder of this Example was prepared in identical fashion to the vitamin supplement of Example 1, with the exception that the final mixture was added to about 7.5 grams of ammonium sulfate (reagent grade) which served as a powder base, instead of the calcium lactate filler material used in Example 1. This vitamin powder may be applied to the plant seeds prior to planting, turned into the soil before planting, sprayed onto the plants while growing, and/or be mixed into a fertilizer which is applied to the soil surrounding the plants.

EXAMPLE 15

In this example, a phytosterol ester vitamin supplement in the form of a powder suitable for spraying or otherwise applying to a plant host was prepared in accordance with the present invention. The vitamin powder of this Example was prepared in identical fashion to the vitamin supplement of Example 2, with the exception that the final mixture was added to about 8 grams of ammonium sulfate (reagent grade) which served as a powder base, instead of the calcium lactate filler material used in Example 2. This vitamin powder may be applied to the plant seeds prior to planting, turned into the soil before planting, sprayed onto the plants while growing, and/or be mixed into a fertilizer which is applied to the soil surrounding the plants.

EXAMPLE 16

In this example, a phytosterol ester vitamin supplement in the form of a powder suitable for spraying or otherwise applying to a plant host was prepared in accordance with the present invention. The vitamin powder of this Example was prepared in identical fashion to the vitamin supplement of Example 3 with the exception that the final mixture was added to about 7.4 grams of ammonium sulfate (reagent grade) which served as a powder base, instead of the calcium lactate filler material used in Example 3. This vitamin powder may be applied to the plant seeds prior to planting, turned into the soil before planting, sprayed onto the plants while growing, and/or be mixed into a fertilizer which is applied to the soil surrounding the plants.

EXAMPLE 17

In this example, a phytosterol ester vitamin supplement in the form of a powder suitable for spraying or otherwise applying to a plant host was prepared in accordance with the present invention. The vitamin powder of this Example was prepared in identical fashion to the vitamin supplement of Example 4, with the exception that the final mixture was added to about 7.4 grams of ammonium sulfate (reagent grade) which served as a powder base, instead of the calcium lactate filler material used in Example 4. This vitamin powder may be applied to the plant seeds prior to planting, turned into the soil before planting, sprayed onto the plants while growing, and/or be mixed into a fertilizer which is applied to the soil surrounding the plants.

EXAMPLE 18

In this example, a phytosterol ester vitamin supplement in the form of a powder suitable for spraying or otherwise applying to a plant host was prepared in accordance with the present invention. The vitamin powder of this Example was prepared in identical fashion to the vitamin supplement of Example 5, with the exception that the final mixture was added to about 7.6 grams of ammonium sulfate (reagent grade) which served as a powder base, instead of the calcium lactate filler material used in Example 5. This vitamin powder may be applied to the plant seeds prior to planting, turned into the soil before planting, sprayed onto the plants while growing, and/or be mixed into a fertilizer which is applied to the soil surrounding the plants.

EXAMPLE 19

In this example, a phytosterol ester vitamin supplement in the form of a powder suitable for spraying or otherwise applying to a plant host was prepared in accordance with the present invention. The vitamin powder of this example was prepared in identical fashion to the vitamin supplement of Example 6, with the exception that the final mixture was added to about 7.8 grams of ammonium sulfate (reagent grade) which served as a powder base instead of the calcium lactate filler material used in Example 6. This vitamin powder may be applied to the plant seeds prior to planting, turned into the soil before planting, sprayed onto the plants while growing, and/or be mixed into a fertilizer which is applied to the soil surrounding the plants.

EXAMPLE 20

In this example, a phytosterol ester vitamin supplement in the form of a liquid was prepared in accordance with the present invention for parenteral administration to animals or for spraying onto plants. The vitamin liquid of this example was prepared in identical fashion to the vitamin supplement of Example 1, with the exception that the final mixture was added to about 5 grams of safflower oil and about 2.2 grams of olive oil which served as a liquid base instead of the calcium lactate carrier material used for the pill of Example 1.

EXAMPLE 21

In this example, a phytosterol ester vitamin supplement in the form of a liquid was prepared in accordance with the present invention for parenteral administration to animals or for spraying onto plants. The vitamin liquid of this examle was prepared in identical fashion to the vitamin supplement of Example 1, with the exception that the final mixture was added to about 7.2 grams of safflower oil and about 10 grams of olive oil which served as a liquid base instead of the calcium lactate carrier material used for the pill of Example 2.

EXAMPLE 22

In this example, a phytosterol ester vitamin supplement in the form of a liquid was prepared in accordance with the present invention for parenteral administration to animals or for spraying onto plants. The vitamin liquid of this example was prepared in identical fashion to the vitamin supplement of Example 1, with the exception that the final mixture was added to about 16 grams of safflower oil and about 11.2 grams of olive oil which served as a liquid base instead of the calcium lactate carrier material used for the pill of Example 3.

EXAMPLE 23

In this example, a phytosterol ester vitamin supplement in the form of a liquid was prepared in accordance with the present invention for parenteral administration to animals or for spraying onto plants. The vitamin liquid of this example was prepared in identical fashion to the vitamin supplement of Example 1, with the exception that the final mixture was added to about 10 grams of safflower oil and about 7.2 grams of olive oil which served as a liquid base instead of the calcium lactate carrier material used for the pill of Example 4.

EXAMPLE 24

In this example, a phytosterol ester vitamin supplement in the form of a liquid was prepared in accordance with the present invention for parenteral administration to animals or for spraying onto plants. The vitamin liquid of this example was prepared in identical fashion to the vitamin supplement of Example 1, with the exception that the final mixture was added to about 30 grams of safflower oil and about 7.2 grams of olive oil which served as a liquid base instead of the calcium lactate carrier material used for the pill of Example 5.

EXAMPLE 25

In this example, a phytosterol ester vitamin supplement in the form of a liquid was prepared in accordance with the present invention for parenteral administration to animals or for spraying onto plants. The vitamin liquid of this example was prepared in identical fashion to the vitamin supplement of Example 1, with the exception that the final mixture was added to about 6 grams of safflower oil and about 1.2 grams of olive oil which served as a liquid base instead of the calcium lactate carrier material used for the pill of Example 6.

EXAMPLE 26-50

In Examples 26-50, phytosterol ester vitamin supplements in accordance with the present invention were prepared identically to the phytosterol ester vitamin supplements of Examples 1-25, respectively, with the exception that, in Examples 2-50, linolenic acid was used in lieu of linoleic acid. In Examples 2-50, approximately the same molar quantities of linolenic acid were used as the molar quantities of linoleic acid employed in Examples 1-25, respectively.

EXAMPLES 51-75

In Examples 51-75, phytosterol ester vitamin supplements in accordance wrth the present invention were prepared identically to the phytosterol ester vitamin supplements of Examples 1-25, respectively, with the exception that, in Examples 51-75, arachidonic acid was used in lieu of linoleic acid. In Examples 51-75, approximately the same molar quantities of arachidonic acid were used as the molar quantities of linoleic acid employed in Examples 1-25, respectively.

Once the phytosterol ester vitamin supplements of the present invention have been administered to an animal or plant, the phytosterol remains bound as a fatty acid ester until the phytosterol ester reaches the cells of the animal or plant. In the cells, the phytosterol ester is then converted into steroids and hormones as well as prostaglandins. A proposed reaction sequence illustrating how the phytosterol esters of the present invention are converted into various steroids and hormones as well as prostaglandins is shown in Equation 2 below, using a linoleic acid ester of stigmasterol as an example:

EQUATION 2

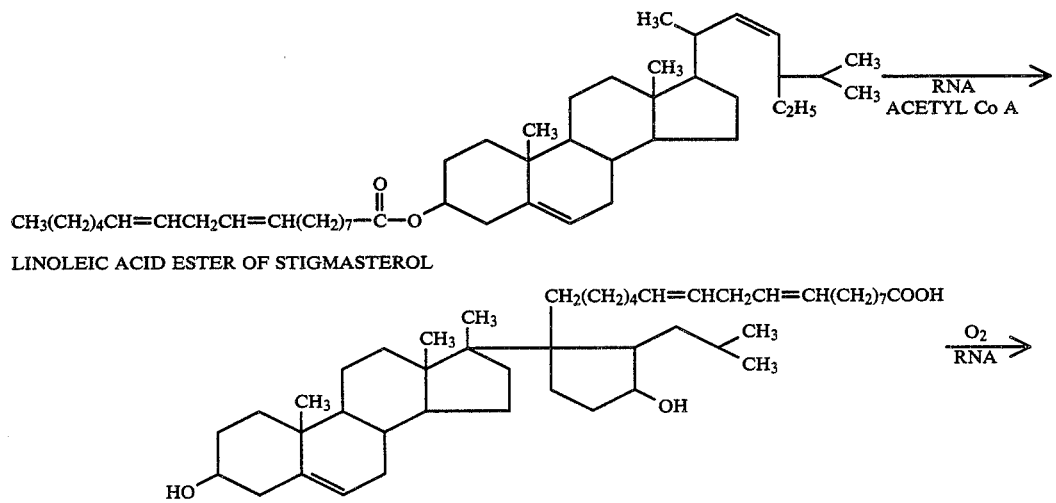

-continued
EQUATION 2

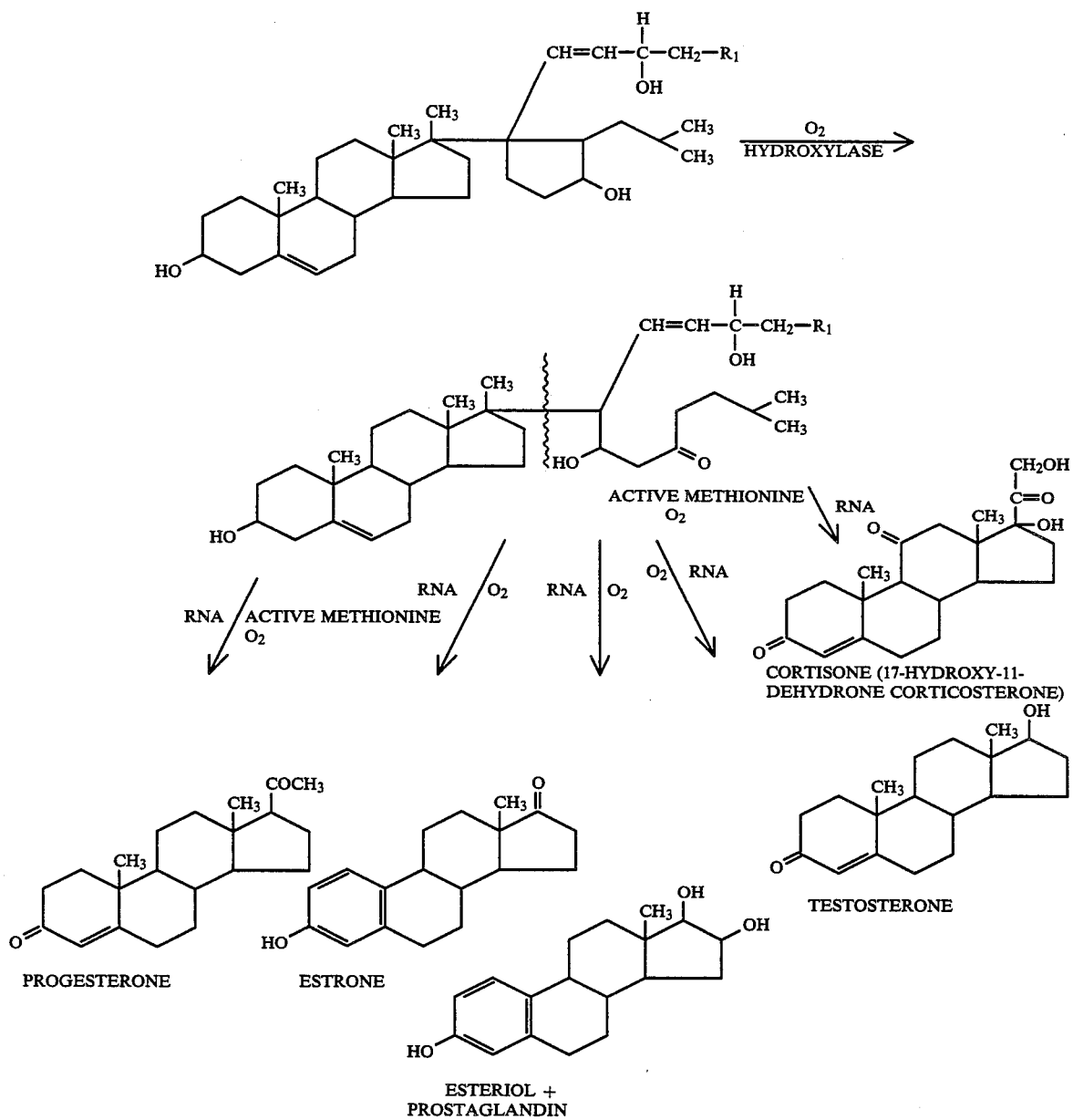

It should be appreciated that the proposed reaction sequence set forth in Equation 2 above is not an attempt to define the precise reaction mechanism involved in producing steroids, hormones, and prostaglandins from phytosterol esters in the present invention. Moreover, it will be appreciated that the exact steroids and hormones formed and the quantities in which they are formed will be determined by the metabollic needs of the animal hosts or plant hosts to which the phytosterol ester vitamin supplements are administered.

Referring to Equation 2 above, $R_1$ represents either —$CH_2CH$=$CH$—$CH_3$ or —$CH_2CH$=$CH$—$CH_2$—$CH$=$CH_2$, depending upon the exact cite of cleavage of the linoleic acid chain. Additionally, it will be appreciated that in the last step of Equation 2, the wavy line indicates where cleavage occurs to form the steroids and hormones of the present invention. During this last step, the right half of the chemical intermediate is released to form a prostaglandin, while the left half of the chemical intermediate is converted into an appropriate steroid or hormone.

The phytosterol esters of the present invention are not converted into steroids, hormones, and prostaglandins in accordance with Equation 2 until the phytosterol esters reach the cells. Upon formation of the steroids and hormones in the cells, the prostaglandins formed are trapped in the cell membranes, along with the other prostaglandins in the cells. The taraxasterol in the vitamin supplements of the present invention controls the release of the prostaglandins so that they are released gradually even through their production is accelerated as the steroids and hormones are produced. Hence, when taraxasterol is used in accordance with the present invention, it serves to control the formation and release of the steroids and hormones. The taraxasterol need not be bound as a fatty acid ester in the present invention, however, introduction of the taraxasterol as a fatty acid ester is presently preferred since the fatty acid portion of the taraxasterol ester serves to increase absorption of the taraxasterol into the body, and inhibits decomposition of the taraxasterol.

B. The Mineral Vitamin Supplements of the Present Invention

The mineral vitamin supplements of the present invention comprise one or more novel substituted fructose compounds, preferably in a pharmaceutically acceptable carrier material. As used herein, the term "substituted fructose" means the general fructose ring structure with a single atom of a particular element being substituted for the number six carbon in the fructose ring structure. Moreover, well-known derivatives of fructose could be used in forming mineral vitamin supplements in accordance with the present invention.

As with the steroid vitamin supplements, many different pharmaceutically acceptable carrier materials are well-known in the art and may be used for purposes of the mineral vitamin supplements of the present invention. Once again, by way of example, carrier materials such as cellulose acetate, phenyl salicylate, corn starch, and fructose may be used as carrier materials The mineral vitamin supplements of the present invention have the following general formula:

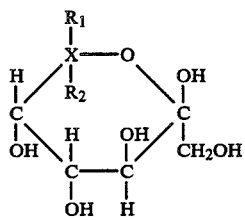

In the above formula, it will be readily appreciated that this formula represents the general ring structure of fructose with an X atom substituted for the number six carbon atom of the fructose ring. X represents an atom which is capable of assuming a +2 or +4 oxidation state. $R_1$ and $R_2$ are both nothing when X is capable of assuming a +2 oxidation state. When X is capable of assuming a +4 oxidation state, one of $R_1$ or $R_2$ will be a hydroxyl group (—OH), and the other of $R_1$ or $R_2$ will be hydrogen (—H).

Although X may be virtually any atom capable of assuming a +2 or +4 oxidation state, for purposes of the vitamin supplements of the present invention, it is preferable to select X from the group of elements having some nutritional value to either animals or plants. For example, X may be selected from the following elements which are capable of assuming a +2 oxidation state and which have nutritional value: calcium (Ca), cobalt (Co), copper (Cu), iron (Fe), magnesium (Mg), manganese (Mn), nickel (Ni), selenium (Se), tin (Sn), and zinc (Zn). Novel compounds formed in accordance with the present invention when X is Ca, Co, Cu, Fe, Mg, Mn, Ni, Se, Sn, or Zn are reproduced below

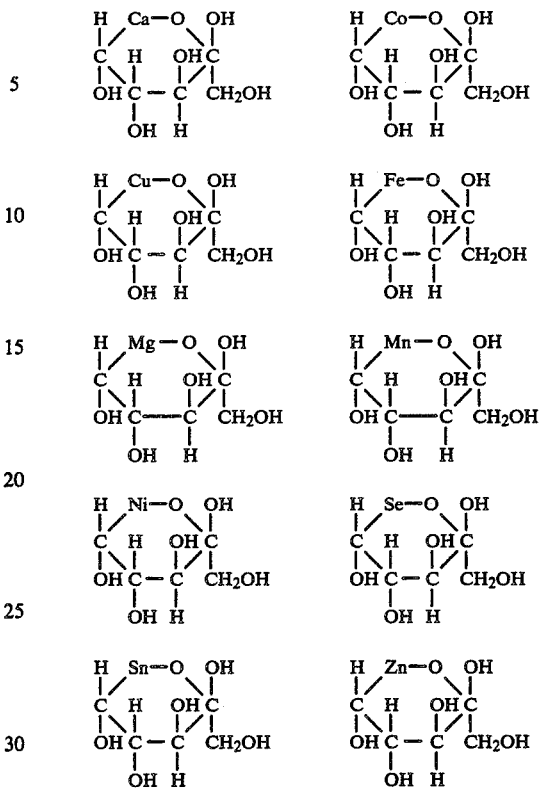

Similarly, X may be selected from the following elements which are capable of assuming a +4 oxidation state and which have some nutritional value: chromium (Cr), manganese (Mn), molybdenum (Mo), phosphorus (P), selenium (Se), and vanadium (V). Novel compounds formed in accordance with the present invention when X is Cr, Mn, Mo, P, Se, or V are reproduced below.

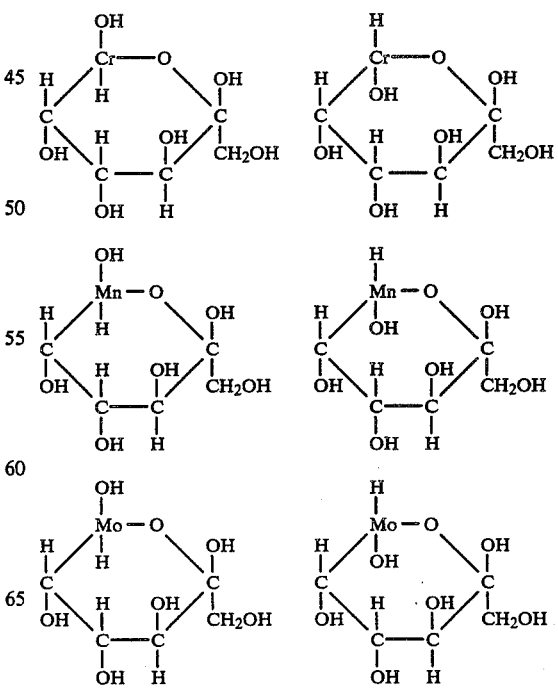

-continued

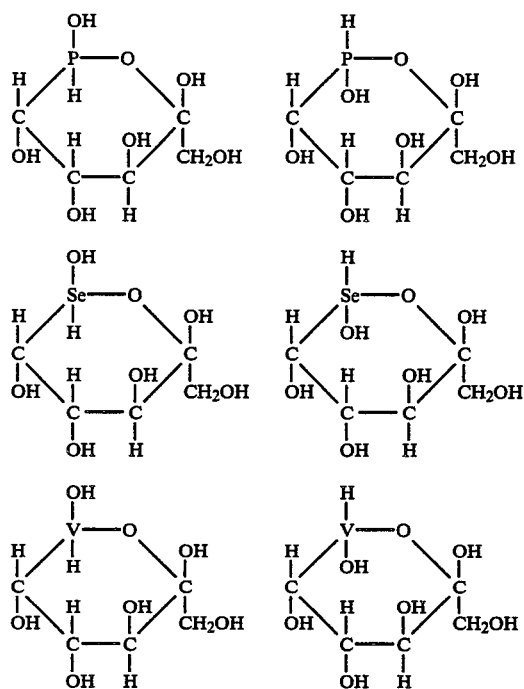

As will be noted above, some elements are capable of assuming both a +2 and +4 oxidation state, e.g., Mn and Se. Hence, as evidenced by the substituted fructose compounds set forth hereinabove for Mn and Se, there are several different configurations which the substituted fructose compounds of the present invention may assume when incorporating Mn and Se.

The determining factor as to whether the novel substituted fructose compound corresponding to the +2 oxidation state or those corresponding to the +4 oxidation state are formed for Mn and Se, is the choice of the reactants for making the compounds. As will be seen hereinafter, when a dihydroxy compound of X is used as a reactant, the substituted fructose compound corresponding to the +2 oxidation state will be formed, while the substituted fructose compounds corresponding to the +4 oxidation state will be formed when a dihydroxy-one compound of X is used as a reactant. When X is an element which forms a +4 oxidation state, nearly equal quantities of the two stereoisomers corresponding to the two possible positions for the hydroxyl group bonded to X are produced, since the energy requirements for forming each stereoisomer are relatively close.

To form a substituted fructose compound within the scope of the present invention, the following procedure is presently preferred. Equal molar quantities of either a dihydroxy compound of X or a dihydroxy-one compound of X and fructose are mixed together. When X is an element capable of forming a +2 oxidation state, the dihydroxy compound of X is mixed with the fructose. When X is an element which is capable of forming a +4 oxidation state, the dihydroxy-one compound of X is mixed with the fructose. Up to about 1 gram of lipase enzyme, about 1 gram of steapsin enzyme, and/or about 1 gram of trypsin enzyme per 100 grams of the substituted fructose compound to be formed may then be blended into the mixture, and the mixture is heated to a temperature of about 15° C.-50° C. for about 1-3 hours.

These amounts of enzyme are based upon National Formulary (N.F.) standards, and will vary if different grades of enzymes are used. More enzyme than the above-given amounts could, of course, be used, but no significant further decrease in reaction time would probably be observed. The mixture is then allowed to cool to a temperature of about 15° C.-30° C. for about 10-60 minutes, and is then reheated to a temperature of about 20° C.-50° C. for about 10-60 minutes in order to ensure that the reaction has gone substantially to completion. The mixture is then allowed to react for a period of about 10-60 minutes to form the substituted fructose compound.

One proposed reaction sequence for forming the novel substituted fructose compounds of the present invention when X is an element capable of assuming a +4 oxidation state is given in Equation 3 below. It will be understood that a similar reaction sequence may be proposed when X is an element capable of assuming a +2 oxidation state.

EQUATION 3

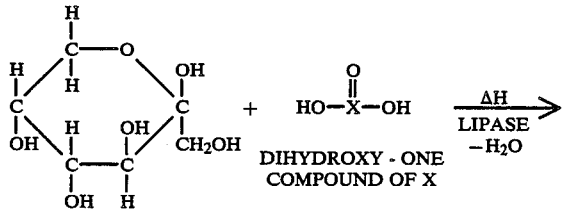

FRUCTOSE

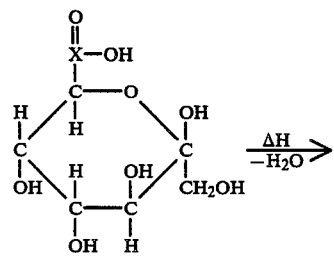

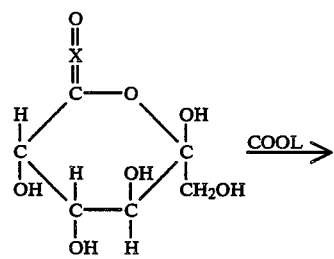

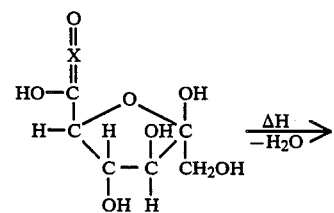

-continued
EQUATION 3

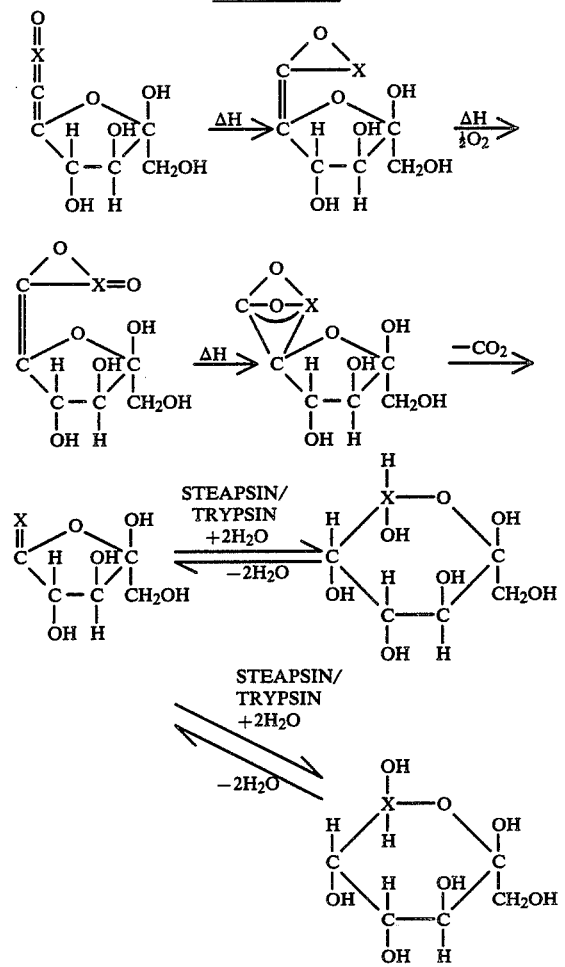

It will be appreciated that, as evidenced by the last reaction step of Equation 3, a chemical equilibrium exists between a five ring heterocyclic structure (the anhydrous form) and a six ring heterocyclic structure (the hydrous form) in the final product. The six member heterocyclic ring structure or hydrous product typically is the most common, however, it will be appreciated that the relative availability of water will determine the relative proportions of the hydrous product and anhydrous product. Hence, it will be appreciated that wherever the six member heterocyclic ring structure is used herein, it will also be deemed to include the five member heterocyclic ring structure, and vice versa. Moreover, it will be seen that there are two possible isomers of the six member heterocyclic ring structure, since the hydroxyl group on the X atom has two possible positions as shown in Equation 3.

It will be appreciated that the respective daily dosages for the mineral vitamin supplements of the present invention will vary according to the mineral (X) used. The following daily dosages in Table 1 below are given to show the maximum amounts per kilogram of animal body weight which would be typically required by an animal. However, it will be appreciated that daily doses different than this may be administered to an animal host, and that the exact preferred daily dosage will necessarily depend upon the specific characteristics of the particular animal treated.

TABLE 1

| Element Incorporated into the Fructose Ring Structure (X) | Maximum Daily Dosage of Compound Administered per Kilogram of Animal Body Weight |
| --- | --- |
| Ca | 150 milligrams |
| Co | 0.5 micrograms |
| Cr | 0.1 milligrams |
| Cu | 0.5 micrograms |
| Fe | 5 milligrams |
| Mg | 150 milligrams |
| Mn | 1.5 milligrams |
| Mo | 0.1 milligrams |
| Ni | 0.5 micrograms |
| P | 150 milligrams |
| Se | 22 milligrams |
| Sn | 1 milligram |
| V | 1 milligram |
| Zn | 1.5 milligrams |

Table 2 below gives the maximum monthly dosages of the compounds of the present invention which are typically needed in order to provide vitamin supplements for plants. Again, it will be appreciated that monthly doses different than this may be administered to a plant host, and that the exact preferred monthly dosage will depend upon the specific characteristics of the particular plant treated.

TABLE 2

| Element Incorporated into the Fructose Ring Structure (X) | Maximum Monthly Dosage of Compound Administered Per Foot of Height of Plant |
| --- | --- |
| Ca | 2 grams |
| Co | 150 milligrams |
| Cr | 2 grams |
| Cu | 150 milligrams |
| Fe | 2 grams |
| Mg | 2 grams |
| Mn | 1.5 grams |
| Mo | 50 milligrams |
| Ni | 400 milligrams |
| P | 2 grams |
| Se | 120 milligrams |
| Sn | 120 milligrams |
| V | 250 milligrams |
| Zn | 1.5 grams |

The novel substituted fructose compounds of the present invention serve to enhance the absorption of the various minerals (represented generically herein by "X") into the body. Since these novel compounds resemble the structure of fructose, they are absorbed by the body as though they were in fact fructose. Moreover, the minerals bound in these novel substituted fructose compounds are not released until they reach the cells of the animal or plant. Upon reaching the cells of the animal or plant, the novel substituted fructose compounds of the present invention decompose to a +2 or +4 ion of X and arabinose. Hence, toxicity is avoided by avoiding, for example, the release of the minerals as ions into the digestive tract and blood stream of an animal.

Certain of the novel substituted fructose compounds of the present invention have particular end uses. For example, the selenium substituted fructose compounds may be used as an antioxidant. These compounds decompose in the animal body to from trimethyl selenonium which is a natural body antioxidant. The iron substituted fructose compound has particular utility in increasing iron absorption and for augmenting the iron concentration in the blood. The chromium, nickel, tin, and zinc substituted fructose compounds are useful in controlling blood sugar levels.

The novel substituted fructose compounds of the present invention have many desirable end uses. Hence, it will be appreciated that the foregoing examples of particular end uses are given solely by way of example, and are in no means intended to be exhaustive of the particular end uses to which these compounds may be applied.

Additionally, the aforementioned minerals which are incorporated into the fructose ring structure of the novel compounds of the present invention and subsequently released in the cells have many utilities once in the cells. For example, these minerals activate different enzymes that are important and often essential to the proper maintenance of the cells of both animals and plants. Some exemplary enzymes and corresponding minerals which may be incorporated into the novel compounds of the present invention to activate those enzymes are given in Table 3 below.

TABLE 3

| Enzymes | Activating Minerals |
|---|---|
| Deaminases (e.g., urease and monoamine oxidase) | Mo, Se, and V |
| Peptidases (e.g., aminopolypeptidase, carboxypolypeptidase, prolinase, and dipeptidase) | Cr, Ni, Sn, and Zn |
| Proteases (e.g., pepsin, trypsin, chymotrypsin, xanthine oxidase, cathepsin, bromelin, and rennin) | Cr, Fe, Mo, Ni, Sn, and Zn |
| Decarboxylating enzymes (e.g., carboxalase and carbonic anhydrase) | Cr, Ni, Sn, and Zn |
| Peroxidases | Ni, Sn and Zn |
| Dehydrogenases | Ni, Sn, V, and Zn |
| Proton donating enzymes derived from thiamine and protein (e.g., insulin and insulinase) | Cr, Ni, Sn, and Zn |
| Esterases, Nucleases, Vitamin L, and succinyl coenzyme A | Ca |
| Certain dehydrogenases, certain peroxidases, and certain oxidases (e.g., xanthine oxidase) | Fe |
| Certain oxidases (e.g., cytochrome oxidases and lysine oxidase), tyrosinase, and uricase | Cu |
| Arginase and pyruvate carboxylase | Mn |
| Hexokinase and mysinogen | Mg |
| Ribonucleotide reductase, glutamemutase, and coenzyme B$_{12}$ | Co |

The mineral vitamin supplements of the present invention may be administered orally, topically, or parenterally to an animal host, while topical administration is generally preferred for plant hosts. Exemplary mineral vitamin supplements within the scope of the present invention which may be employed in these various modes of application are given below.

EXAMPLE 76

In this example, a mineral vitamin supplement in the form of a pill incorporating a calcium (+2) substituted fructose compound was prepared in accordance with the present invention for oral administration to animals.

First, a saturated solution or sludge (having a concentration of about 1 gram Ca(OH)$_2$/ml glycerol) of calcium hydroxide in glycerol was prepared. Next, about 18 grams of fructose and about 15 grams of the saturated calcium hydroxide solution were mixed together, these quantities roughly estimating equal molar quantities of fructose and calcium. To this mixture was added about 0.1 grams of steapsin enzyme, and the resultant mixture was heated to a temperature of about 45° C. for a period of about two hours. After heating, the mixture was cooled to about 25° C. for about 30 minutes. After cooling the mixture, the mixture was then reheated to about 45° C. for about 40 minutes, and allowed to react for about an additional 15 minutes thereafter. The resultant compound was a calcium (+2) substituted fructose compound according to the formula reproduced below:

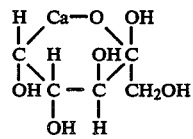

Subsequently, the calcium (+2) substituted fructose compound was included into a pill by mixing about 250 milligrams of the calcium substituted fructose compound with about 250 milligrams of calcium lactate, and compressing the mixture into a pill. About 2 of the mineral vitamin pills prepared in accordance with this example should be administered to the average human adult on a daily basis.

The substituted fructose compounds made in each of Examples 77–85, 92–101, 108–117, and 124–133 which follow are reproduced below:

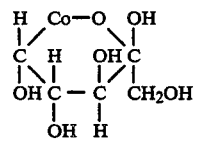

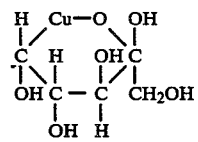 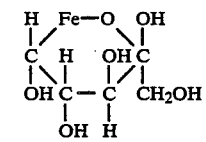

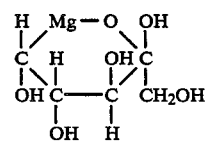 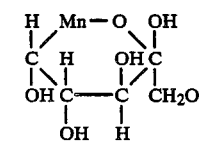

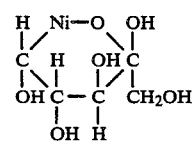 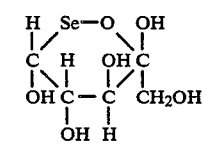

-continued

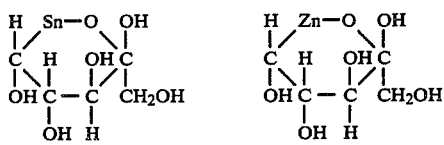

Similarly, the substituted fructose compounds made in each of Examples 86–91, 102–107, 118–123, and 134–139 which follow are reproduced below:

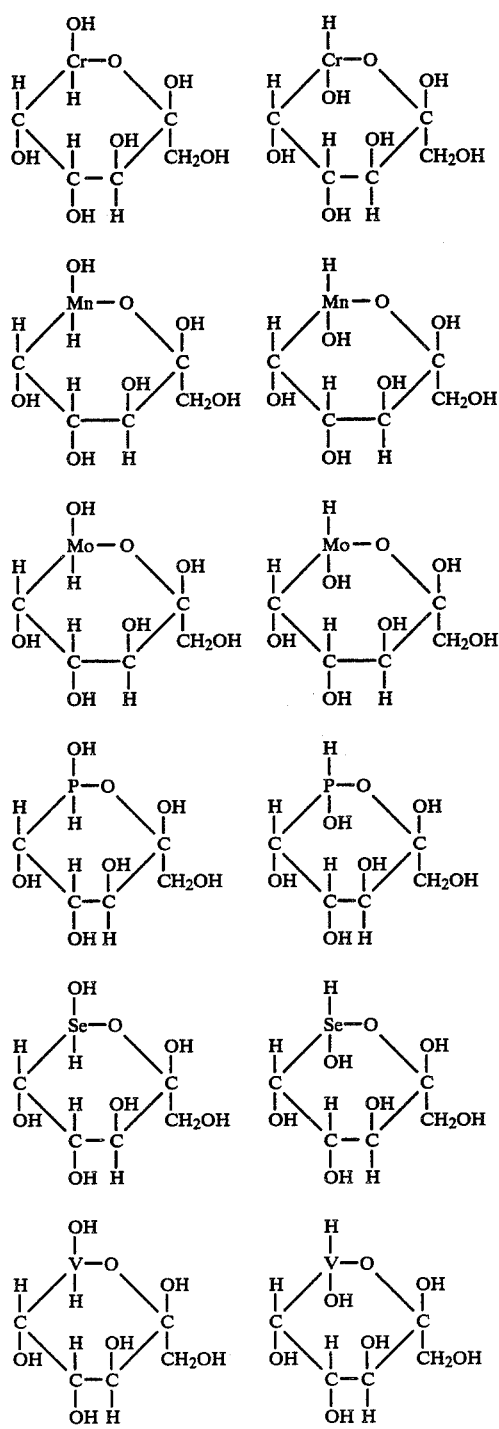

EXAMPLE 77

In this example, a mineral vitamin supplement in the form of a pill incorporating a cobalt (+2) substituted fructose compound was prepared in accordance with the present invention for oral administration to animals. This example is identical to Example 76 except that about 18.6 grams of a saturated cobalt hydroxide in glycerol solution or sludge (having a concentration of about 1 gram Co(OH)$_2$/ml glycerol) were used instead of the calcium hydroxide solution of Example 76, and only about 5 micrograms of the resultant cobalt (+2) substituted fructose compound were added to about 100 milligrams of calcium lactate and pressed into a pill.

EXAMPLE 78

In this example, a mineral vitamin supplement in the form of a pill incorporating a copper (+2) substituted fructose compound was prepared in accordance with the present invention for oral administration to animals. This example is identical to Example 76 except that about 19.6 grams of a saturated copper hydroxide in glycerol solution or sludge (having a concentration of about 1 gram Cu(OH)$_2$/ml glycerol) were used instead of the calcium hydroxide solution of Example 76, and only about 5 micrograms of the resultant copper (+2) substituted fructose compound were added to about 100 milligrams of calcium lactate and pressed into a pill.

EXAMPLE 79

In this example, a mineral vitamin supplement in the form of a pill incorporating a iron (+2) substituted fructose compound was prepared in accordance with the present invention for oral administration to animals. This example is identical to Example 76 except that about 18 grams of a saturated iron II hydroxide in glycerol solution or sludge (having a concentration of about 1 gram Fe(OH)$_2$/ml glycerol) were used instead of the calcium hydroxide solution of Example 76, and only about 10 milligrams of the resultant iron (+2) substituted fructose compound were added to about 240 milligrams of calcium lactate and pressed into a pill.

EXAMPLE 80

In this example, a mineral vitamin supplement in the form of a pill incorporating a magnesium (+2) substituted fructose compound was prepared in accordance with the present invention for oral administration to animals. This example is identical to Example 76 except that about 11.7 grams of a saturated magnesium hydroxide in glycerol solution or sludge (having a concentration of about 1 gram Mg(OH)$_2$/ml glycerol) were used instead of the calcium hydroxide solution of Example 76. Similar to Example 76, about 250 milligrams of the resultant magnesium (+2) substituted fructose compound were added to about 250 milligrams of calcium lactate and pressed into a pill.

EXAMPLE 81

In this example, a mineral vitamin supplement in the form of a pill incorporating a manganese (+2) substituted fructose compound was prepared in accordance with the present invention for oral administration to animals. This example is identical to Example 76 except that about 17.6 grams of a saturated manganese hydroxide in glycerol solution or sludge (having a concentration of about 1 gram Mn(OH)$_2$/ml glycerol) were used instead of the calcium hydroxide solution of Example 76, and only about 6 milligrams of the resultant manganese (+2) substituted fructose compound were added to about 244 milligrams of calcium lactate and pressed into a pill.

EXAMPLE 82

In this example, a mineral vitamin supplement in the form of a pill incorporating a nickel (+2) substituted fructose compound was prepared in accordance with the present invention for oral administration to animals. This example is identical to Example 76 except that about 18.6 grams of a saturated nickel hydroxide in glycerol solution or sludge (having a concentration of about 1 gram $Ni(OH)_2$/ml glycerol) were used instead of the calcium hydroxide solution of Example 76, and only about 5 milligrams of the resultant nickel (+2) substituted fructose compound were added to about 245 milligrams of calcium lactate and pressed into a pill.

EXAMPLE 83

In this example, a mineral vitamin supplement in the form of a pill incorporating a selenium (+2) substituted fructose compound was prepared in accordance with the present invention for oral administration to animals. This example is identical to Example 76 except that about 65 grams of a saturated selenious acid (the dihydroxy-one of selenium) in water solution (having a concentration of about 2 grams $H_2SeO_3$/ml water) were used instead of the calcium hydroxide solution of Example 76, and the resultant selenium (+4) substituted fructose compound was reduced to a selenium (+2) fructose compound by mixing the compound with about 0.5 ml of 1N. HCl and allowing the compound to dry at room temperature (about 20° C.) for about 2 hours. Although it is possible to make the selenium (+2) substituted fructose compound directly without first making the selenium (+4) substituted fructose compound, for ease of procedure, it is presently preferable to first manufacture the selenium (+4) substituted fructose compound and then reduce it to the selenium (+2) substituted fructose compound. Only about 2 milligrams of the resultant selenium (+2) substituted fructose compound were added to about 98 milligrams of calcium lactate and pressed into a pill.

EXAMPLE 84

In this example, a mineral vitamin supplement in the form of a pill incorporating a tin (+2) substituted fructose compound was prepared in accordance with the present invention for oral administration to animals. This example is identical to Example 76 except that about 31 grams of a saturated tin hydroxide in glycerol solution or sludge (having a concentration of about 1 gram $SnO.H_2O$/ml glycerol) were used instead of the calcium hydroxide solution of Example 76, and only about 10 milligrams of the resultant tin (+2) substituted fructose compound were added to about 90 milligrams of calcium lactate and pressed into a pill.

EXAMPLE 85

In this example, a mineral vitamin supplement in the form of a pill incorporating a zinc (+2) substituted fructose compound was prepared in accordance with the present invention for oral administration to animals. This example is identical to Example 76 except that about 20 grams of a saturated zinc hydroxide in glycerol solution or sludge (having a concentration of about 1 gram $Zn(OH)_2$/ml glycerol) were used instead of the calcium hydroxide solution of Example 76, and only about 8 milligrams of the resultant zinc (+2) substituted fructose compound were added to about 92 milligrams of calcium lactate and pressed into a pill.

EXAMPLE 86

In this example, a mineral vitamin supplement in the form of a pill incorporating a chromium (+4) substituted fructose compound was prepared in accordance with the present invention for oral administration to animals. First, about 10 grams of chromium trioxide, about 10 milliliters of glycerol, and about 0.5 milliliters of hydrochloric acid (HCl) were mixed together to form about 20 milliliters of a saturated chromium dihydroxy-one in glycerol solution or sludge (having a concentration of about 1 gram $CrO(OH)_2$/ml glycerol). This example is then identical to Example 76 except that about 20 grams of the saturated chromium dihydroxy-one in glycerol solution or sludge were used instead of the calcium hydroxide solution of Example 76, and only about 100 micrograms of the resultant chromium (+4) substituted fructose compound were added to about 100 milligrams of calcium lactate and pressed into a pill.

EXAMPLE 87

In this example, a mineral vitamin supplement in the form of a pill incorporating a manganese (+4) substituted fructose compound was prepared in accordance with the present invention for oral administration to animals. First, about 10.5 grams of manganese trioxide, about 10.5 milliliters of glycerol, and about 0.5 milliliters of hydrochloric acid were mixed together to form a saturated manganese dihydroxy-one in glycerol solution or sludge (having a concentration of about 1 gram $MnO(OH)_2$/ml glycerol). This example is then identical to Example 76 except that about 21 grams of the saturated manganese dihydroxy-one in glycerol solution or sludge were used instead of the calcium hydroxide solution of Example 76, and only about 6 milligrams of the resultant manganese (+4) substituted fructose compound were added to about 94 milligrams of calcium lactate and pressed into a pill.

EXAMPLE 88

In this example, a mineral vitamin supplement in the form of a pill incorporating a molybdenum (+4) substituted fructose compound was prepared in accordance with the present invention for oral administration to animals. First, about 14.6 grams of molybdenum trioxide, about 14.6 milliliters of glycerol, and about 0.5 milliliters of hydrochloric acid were mixed together to form a saturated molybdenum dihydroxy-one in glycerol solution or sludge (having a concentration of about 1 gram $MoO(OH)_2$/ml glycerol). This example is then identical to Example 76 except that about 29.2 grams of the saturated molybdenum dihydroxy-one in glycerol solution or sludge were used instead of the calcium hydroxide solution of Example 76, and only about 2 milligrams of the resultant molybdenum (+4) substituted fructose compound were added to about 98 milligrams of calcium lactate and pressed into a pill.

EXAMPLE 89

In this example, a mineral vitamin supplement in the form of a pill incorporating a phosphorous (+4) substituted fructose compound was prepared in accordance with the present invention for oral administration to animals. First, about 8.1 grams of phosphorous acid (phosphorous acid is the dihydroxy-one of phosphorous), having a concentration of about 90% phosphorous acid by weight (with the remainder being water), were added to about 8.1 milliliters of glycerol to form a saturated phosphorous acid in glycerol solution (having a concentration of about 1 gram $H_3PO_3$/ml glycerol). This example is then identical to Example 76 except that about 16.2 grams of the saturated phosphorous acid in glycerol solution were used instead of the calcium hydroxide solution of Example 76. Similar to Example 76, about 250 milligrams of the resultant phosphorous (+4) substituted fructose compound were added to about 250 milligrams of calcium lactate and pressed into a pill.

EXAMPLE 90

In this example, a mineral vitamin supplement in the form of a pill incorporating a selenium (+4) substituted fructose compound was prepared in accordance with the present invention for oral administration to animals. This example is identical to Example 76 except that about 65 grams of a saturated selenious acid in water solution (having a concentration of about 2 grams $H_2SeO_3$/ml water) were used instead of the calcium hydroxide solution of Example 76, and only about 2 milligrams of the resultant selenium (+4) substituted fructose compound were added to about 98 milligrams of calcium lactate and pressed into a pill.

EXAMPLE 91

In this example, a mineral vitamin supplement in the form of a pill incorporating a vanadium (+4) substituted fructose compound was prepared in accordance with the present invention for oral administration to animals. First, about 15 grams of vanadium trioxide, about 15 milliliters of glycerol, and about 0.5 milliliters of hydrochloric acid were mixed together to form a saturated vanadium dihydroxy-one in glycerol solution or sludge (having a concentration of about 1 gram $VO(OH)_2$/ml glycerol). This example is then identical to Example 76 except that about 30 grams of the saturated vanadium dihydroxy-one in glycerol solution or sludge were used instead of the calcium hydroxide solution of Example 76, and only about 6 milligrams of the resultant vanadium (+4) substituted fructose compound were added to about 94 milligrams of calcium lactate and pressed into a pill.

EXAMPLE 92

In this example, a mineral vitamin supplement in the form of a cream was prepared incorporating a calcium (+2) substituted fructose compound in accordance with the present invention for topical administration to animals. First, a calcium (+2) substituted fructose compound was prepared in accordance with Example 76. However, in this example, about 1 gram of the calcium (+2) substituted fructose compound formed was added to about 50 grams of palmitic acid which served as a cream base, in lieu of the calcium lactate used in Example 76. The calcium vitamin cream thus prepared may be topically administered to a human or other animal on a daily basis.

EXAMPLE 93

In this example, a mineral vitamin supplement in the form of a cream was prepared incorporating a cobalt (+2) substituted fructose compound in accordance with the present invention for topical administration to animals. First, a cobalt (+2) substituted fructose compound was prepared in accordance with Example 77. However, in this example, about 0.01 grams of the cobalt (+2) substituted fructose compound formed were added to about 20 grams of palmitic acid which served as a cream base, in lieu of the calcium lactate used in Example 77. The cobalt vitamin cream thus prepared may be topically administered to a human or other animal on a daily basis.

EXAMPLE 94

In this example, a mineral vitamin supplement in the form of a cream was prepared incorporating a copper, (+2) substituted fructose compound in accordance with the present invention for topical administration to animals. First, a copper (+2) substituted fructose compound was prepared in accordance with Example 78. However, in this example, about 1 gram of the copper (+2) substituted fructose compound formed was added to about 100 grams of palmitic acid which served as a cream base, in lieu of the calcium lactate used in Example 78. The copper vitamin cream thus prepared may be topically administered to a human or other animal on a daily basis.

EXAMPLE 95

In this example, a mineral vitamin supplement in the form of a cream was prepared incorporating a iron (+2) substituted fructose compound in accordance with the present invention for topical administration to animals. First, a iron (+2) substituted fructose compound was prepared in accordance with Example 79. However, in this example, about 5 grams of the iron (+2) substituted fructose compound formed were added to about 100 grams of palmitic acid which served as a cream base, in lieu of the calcium lactate used in Example 79. The iron vitamin cream thus prepared may be topically administered to a human or other animal on a daily basis.

EXAMPLE 96

In this example, a mineral vitamin supplement in the form of a cream was prepared incorporating a magnesium (+2) substituted fructose compound in accordance with the present invention for topical administration to animals. First, a magnesium (+2) substituted fructose compound was prepared in accordance with Example 80. However, in this example, about 2.5 grams of the magnesium (+2) substituted fructose compound formed were added to about 97.5 grams of palmitic acid which served as a cream base, in lieu of the calcium lactate used in Example 80. The magnesium vitamin cream thus prepared may be topically administered to a human or other animal on a daily basis.

EXAMPLE 97

In this example, a mineral vitamin supplement in the form of a cream was prepared incorporating a manganese (+2) substituted fructose compound in accordance with the present invention for topical administration to animals. First, a manganese (+2) substituted fructose compound was prepared in accordance with Example 81. However, in this example, about 0.1 grams of the manganese (+2) substituted fructose compound formed were added to about 100 grams of palmitic acid which served as a cream base, in lieu of the calcium lactate used in Example 81. The manganese vitamin cream thus prepared may be topically administered to a human or other animal on a daily basis.

EXAMPLE 98

In this example, a mineral vitamin supplement in the form of a cream was prepared incorporating a nickel (+2) substituted fructose compound in accordance with the present invention for topical administration to animals. First, a nickel (+2) substituted fructose compound was prepared in accordance with Example 82. However, in this example, about 0.1 grams of the nickel (+2) substituted fructose compound formed were added to about 100 grams of palmitic acid which served as a cream base, in lieu of the calcium lactate used in Example 82. The nickel vitamin cream thus prepared may be topically administered to a human or other animal on a daily basis.

EXAMPLE 99

In this example, a mineral vitamin supplement in the form of a cream was prepared incorporating a selenium (+2) substituted fructose compound in accordance with the present invention for topical administration to animals. First, a selenium (+2) substituted fructose compound was prepared in accordance with Example 83. However, in this example, about 2 grams of the selenium (+2) substituted fructose compound formed were added to about 98 grams of palmitic acid which served as a cream base, in lieu of the calcium lactate used in Example 83. The selenium vitamin cream thus prepared may be topically administered to a human or other animal on a daily basis.

EXAMPLE 100

In this example, a mineral vitamin supplement in the form of a cream was prepared incorporating a tin (+2) substituted fructose compound in accordance with the present invention for topical administration to animals. First, a tin (+2) substituted fructose compound was prepared in accordance with Example 84. However, in this example, about 1 gram of the tin (+2) substituted fructose compound formed was added to about 99 grams of palmitic acid which served as a cream base, in lieu of the calcium lactate used in Example 84. The tin vitamin cream thus prepared may be topically administered to a human or other animal on a daily basis.

EXAMPLE 101

In this example, a mineral vitamin supplement in the form of a cream was prepared incorporating a zinc (+2) substituted fructose compound in accordance with the present invention for topical administration to animals. First, a zinc (+2) substituted fructose compound was prepared in accordance with Example 85. However, in this example, about 1 gram of the zinc (+2) substituted fructose compound formed was added to about 99 grams of palmitic acid which served as a cream base, in lieu of the calcium lactate used in Example 85. The zinc vitamin cream thus prepared may be topically administered to a human or other animal on a daily basis.

EXAMPLE 102

In this example, a mineral vitamin supplement in the form of a cream was prepared incorporating a chromium (+4) substituted fructose compound in accordance with the present invention for topical administration to animals. First, a chromium (+4) substituted fructose compound was prepared in accordance with Example 86. However, in this example, about 1 gram of the chromium (+4) substituted fructose compound formed was added to about 99 grams of palmitic acid which served as a cream base, in lieu of the calcium lactate used in Example 86. The chromium vitamin cream thus prepared may be topically administered to a human or other animal on a daily basis.

EXAMPLE 103

In this example, a mineral vitamin supplement in the form of a cream was prepared incorporating a manganese (+4) substituted fructose compound in accordance with the present invention for topical administration to animals. First, a manganese (+4) substituted fructose compound was prepared in accordance with Example 87. However, in this example, about 1 gram of the manganese (+4) substituted fructose compound formed was added to about 99 grams of palmitic acid which served as a cream base, in lieu of the calcium lactate used in Example 87. The manganese vitamin cream thus prepared may be topically administered to a human or other animal on a daily basis.

EXAMPLE 104

In this example, a mineral vitamin supplement in the form of a cream was prepared incorporating a molybdenum (+4) substituted fructose compound in accordance with the present invention for topical administration to animals. First, a molybdenum (+4) substituted fructose compound was prepared in accordance with Example 88. However, in this example, about 1 gram of the molybdenum (+4) substituted fructose compound formed was added to about 99 grams of palmitic acid which served as a cream base, in lieu of the calcium lactate used in Example 88. The molybdenum vitamin cream thus prepared may be topically administered to a human or other animal on a daily basis.

EXAMPLE 105

In this example, a mineral vitamin supplement in the form of a cream was prepared incorporating a phosphorous (+4) substituted fructose compound in accordance with the present invention for topical administration to animals. First, a phosphorous (+4) substituted fructose compound was prepared in accordance with Example 89. However, in this example, about 10 grams of the phosphorous (+4) substituted fructose compound formed were added to about 90 grams of palmitic acid which served as a cream base, in lieu of the calcium lactate used in Example 89. The phosphorous vitamin cream thus prepared may be topically administered to a human or other animal on a daily basis.

EXAMPLE 106

In this example, a mineral vitamin supplement in the form of a cream was prepared incorporating a selenium (+4) substituted fructose compound in accordance with the present invention for topical administration to animals. First, a selenium (+4) substituted fructose compound was prepared in accordance with Example 90. However, in this example, about 2 grams of the selenium (+4) substituted fructose compound formed were added to about 98 grams of palmitic acid which served as a cream base, in lieu of the calcium lactate used in Example 90. The selenium vitamin cream thus prepared may be topically administered to a human or other animal on a daily basis.

EXAMPLE 107

In this example, a mineral vitamin supplement in the form of a cream was prepared incorporating a vanadium (+4) substituted fructose compound in accordance with the present invention for topical administration to animals. First, a vanadium (+4) substituted fructose compound was prepared in accordance with Example 91. However, in this example, about 0.1 grams of the vanadium (+4) substituted fructose compound formed were added to about 100 grams of palmitic acid which served as a cream base, in lieu of the calcium lactate used in Example 91. The vanadium vitamin cream thus prepared may be topically administered to a human or other animal on a daily basis.

EXAMPLES 108-123

In these examples, mineral vitamin supplements in the form of powders suitable for spraying or otherwise applying to plant hosts were prepared incorporating the substituted fructose compounds prepared in accordance with Examples 76-91. Examples 108-123 are thus identical to Examples 76-91, respectively, with the exception that in Examples 108-123, about 5 grams of the substituted fructose compound of each example was added to about 95 grams of ammonium sulfate instead of the calcium lactate filler material used in Examples 76-91.

EXAMPLES 124-139

In these examples, mineral vitamin supplements in the form of liquids were prepared in accordance with the present invention for parenteral administration to animals or for spraying onto plants. Examples 124-139 are identical to Examples 76-91, respectively, with the exception that in Examples 124, 127-133, and 135-139, about 500 milligrams of the substituted fructose compound of these examples, and in Examples 125-126 and 134 about 50 micrograms of the substituted fructose compound of these examples, were added to about 8 grams of safflower oil and about 2 grams of olive oil instead of the calcium lactate filler material used in Examples 76-91.

C. The Diet Pills and Diet Vitamin Supplements of the Present Invention

The diet pills and diet vitamin supplements of the present invention comprise antitrypsin enzyme, preferably in a pharmaceutically acceptable enzyme stabilizing material as a carrier. Many different pharmaceutically acceptable enzyme stabilizing materials are well-known in the art and may be used for purposes of the carrier material in the diet pills and diet vitamin supplements of the present invention.

By way of example, enzyme stabilizing materials such as calcium lactate, calcium propionate, ascorbic acid, and Vitamin E, may be used as carrier materials. The important feature of the carrier material used is that it protects the antitrypsin enzyme from decomposition by, for example, hydrolysis or oxidation. Any carrier material which will adequately protect the antitrypsin enzyme will be suitable for purposes of the present invention.

Antitrypsin enzyme may be extracted from such natural sources as jack beans, soy beans, animal blood plasma, lima beans, beef pancreas, chicken egg whites, or turkey egg whites. Procedures for isolating antitrypsin enzyme are well known in the art, for example, chromatography is often used. As suggested by its name, antitrypsin serves to inhibit the action of trypsin, an enzyme which is important in the digestion process. For example, trypsin cleaves protein chains where a lysine-arginine amino acid sequence pair occurs, cleaves sugar esters from a protein chain, and further serves to hydrolyze polysaccharides.

Antitrypsin thus serves to inhibit such cleavage and hydrolysis by inhibiting the action of trypsin in the digestion process. Hence, antitrypsin serves to inhibit the digestion and absorption of, for example, carbohydrates into the body of an animal. The carbohydrates not utilized by the animal are then passed through normal excretory channels.

Thus, by including antitrypsin enzyme into a diet pill in accordance with the present invention, a diet pill is provided whereby normal caloric intake may be maintained by an individual, while the actual absorption of carbohydrates is substantially decreased. As a result, the dieting individual need not starve himself and in the process deprive himself of needed nutrients, but rather may lose weight while maintaining normal caloric intake.

In the diet pills and diet vitamin supplements of the present invention, amylase inhibitor may also be included along with the antitrypsin enzyme. Amylase inhibitor inhibits the action of the enzyme amylase. Since amylase acts to break down polysaccharides, amylase inhibitor discourages the breakdown of polysaccharides. Hence, similar to the action of antitrypsin, amylase inhibitor acts to decrease the absorption of carbohydrates ingested by an individual, and may therefore also serve as a diet aid.

Amylase inhibitor may be extracted from such natural sources as wheat and soya. Again, processes for so extracting and isolating amylase inhibitor are well-known, and include, for example, chromatography. Moreover, most naturally occurring antitrypsin which is extracted from the sources mentioned herein, also contains up to 5% weight of amylase inhibitor. Hence, amylase inhibitor may also generally be obtained from the same natural sources as antitrypsin.

For purposes of the present invention, amylase inhibitor may be added in quantities of up to about 80% by weight of the antitrypsin. Although 100% amylase inhibitor could be used in a diet pill, there are several reasons why this is not desirable: (1) gas problems, (2) diarrhea, and (3) amylase inhibitor is much more expensive than antitrypsin. On the other hand, amylase inhibitor serves to stabilize the overall strength of antitrypsin, and it is thus presently preferable to make diet pills in accordance with the present invention having an amylase inhibitor/antitrypsin weight ratio of about 1:50 to about 1:20.

To form a diet pill in accordance with the present invention, antitrypsin enzyme, and if desired, amylase inhibitor are gently mixed into the carrier material and pressed into a pill. Such procedure may be done, for example, at room temperature and pressure.

For purposes of the diet pills and diet vitamin supplements of the present invention, it has been found that inclusion of enough antitrypsin in the diet pill to provide a daily dosage of up to about 0.2 micrograms of antitrypsin per kilogram of animal body weight, produces the desirable effects of the present invention. Similarly, inclusion of enough amylase inhibitor in the diet pill to provide a daily dosage of up to about 0.02 micrograms of amylase inhibitor per kilogram of animal body weight, serves to produce the desirable effects of the present invention.

It will, of course, again be recognized that daily dosages larger than the foregoing may be administered to an animal, and that the exact daily dosage will depend upon the nature, size, metabolism, and other characteristics of the animal treated. Typically, the inclusion of much larger amounts of antitrypsin and amylase inhibitor then the foregoing dosages only result in dosages which cannot be fully utilized by the animal. However, such larger dosages are not generally harmful if administered.

The foregoing daily dosages for antitrypsin are based upon antitrypsin which has a potency defined as follows. These dosages correspond to antitrypsin having a potency such that 1 milligram of the antitrypsin will inhibit approximately 0.6 milligrams of trypsin, where the trypsin has an activity of about 10,000 benzyl arginine ethyl ester (BAEE) units per milligram of protein.

The foregoing daily dosages for amylase inhibitor are based on amylase inhibitor having a potency such that 1 milligram of the amylase inhibitor represents from about 2,000 to about 3,000 units of activity. One unit of amylase inhibitor activity is defined as the activity needed to reduce the activity of two units of human saliva amylase by 50% at 25° C. A unit of activity of human saliva amylase is defined as the activity required to liberate one milligram of maltose from starch in three minutes at a temperature of 37° C. and a pH of 6.9.

The diet pills and diet vitamin supplements of the present invention should be administered orally. An exemplary diet pill within the scope of the present invention is given below.

EXAMPLE 140

In this example, a diet pill was prepared in accordance with the present invention for oral administration to animals. The vitamin pill of this example was prepared as follows. About 1 microgram of antitrypsin enzyme was mixed together with about 0.05 micrograms of amylase inhibitor. To this mixture was added about 1 milligram of sodium ascorbate and about 9 grams of cellulose acetate which served as a filler material. The mixture was blended well, and subsequently, another 100 milligrams of cellulose acetate was added and thoroughly blended into the mixture. This mixture was then pressed into ten pills, with each pill representing a typical daily dosage of antitrypsin and amylase inhibitor for the individual treated.

It will be appreciated that the antitrypsin and amylase inhibitor which are incorporated into the diet pills of the present invention may also be incorporated into various vitamin supplements including those phytosterol ester vitamin supplements and mineral vitamin supplements disclosed and claimed herein. Similarly, it will be appreciated that numerous combinations of the phytosterol ester vitamin supplements, mineral vitamin supplements, and diet pills and diet vitamin supplements disclosed and claimed herein may be formulated to achieve a variety of nutritive and dietetic purposes. Other examples of possible combinations of the vitamin supplements and diet pills of the present invention with other known vitamin constituents are set forth hereinafter.

D. Other Vitamin Supplements and Diet Vitamin Supplements of the Present Invention The following examples are given to show exemplary combinations of the phytosterol ester vitamin supplements, mineral vitamin supplements, and diet pills of the present invention, in combination with nutritive substances which are used in existing vitamin supplements. It will be recognized that the foregoing examples are clearly not exhaustive of all the possible combinations which are possible in formulating vitamin supplements within the scope of the present invention. Rather, these examples are given in order to illustrate the numerous possibilities for formulating vitamin supplements in accordance with the present invention.

EXAMPLE 141

In this Example, a vitamin supplement in the form of a pill was prepared in accordance with the present invention for oral administration to animals. The vitamin supplement of this example contained phytosterol ester vitamins, mineral vitamins, and diet vitamins prepared in accordance with the present invention. The vitamin supplement of this example also contained additional nutritive substances and vitamins so as to form a complete diet vitamin supplement.

The vitamin supplement of this example was prepared at room temperature (about 20° C.) and room pressure. In the preparation of about 30 grams of the vitamin supplement of this example, the following ingredients were used in the proportions given below:

| Ingredient | Amount |
| --- | --- |
| Vitamin A* | 18 milligrams (60,000 I.U.) |
| Vitamin E | 300 milligrams (300 I.U.) |
| Inositol | 1 gram |
| Safflower Oil | 5.64 grams |
| Liver (whole dried) | 750 milligrams |
| Sitosterol | 900 milligrams |
| Stigmasterol | 525 milligrams |
| Taraxasterol | 5 milligrams |
| Cephalin | 101.3 micrograms |
| Sphingomyelin | 56.3 micrograms |
| Lecithin | 195 micrograms |
| Fructose | 554 milligrams |
| Corn Starch | 250 milligrams |
| Lipoxidase | 2.25 milligrams (60,000 units/mg) |
| Urease | 20.25 milligrams (500 units/g) |
| Protease | 22.5 milligrams (8 units/mg) |
| Antitrypsin enzyme | 22.5 micrograms |
| Vitamin $D^3$ | 100 micrograms (4000 I.U.) |
| Vitamin $B^1$ | 150 milligrams |
| Vitamin $B^2$ | 150 milligrams |
| Vitamin $B^3$ | 750 milligrams |
| Vitamin $B^4$ | 60 milligrams |
| Vitamin $B^5$ | 180 milligrams |
| Vitamin $B^6$ | 210 milligrams |
| Vitamin $B^{12}$ | 150 micrograms |
| Vitamin C | 1.35 grams |
| Folic acid | 4 milligrams |
| Potassium iodide | 1.95 milligrams |
| Zinc sulfate | 186.7 milligrams |
| Copper sulfate | 75.36 milligrams |
| Choline chloride | 1 gram |
| Colamine | 1 gram |
| Manganese sulfate | 184 milligrams |
| Potassium chloride | 1.907 grams |
| Calcium phosphate (dibasic) | 4.8 grams |
| Sodium chromate (VI) | 4.5 milligrams |

-continued

| Ingredient | Amount |
| --- | --- |
| Stanous chloride | 159.74 milligrams |
| Nickel sulfate | 44.8 milligrams |
| Sodium molybdate (VI) | 12.61 milligrams |
| Magnesium oxide | 1.66 grams |
| Iron II fumarate | 548 milligrams |
| Sodium vanadate (V) | 38.1 milligrams |
| Para-aminobenzoic acid | 300 milligrams |
| Citrus bioflavonoids | 1 gram |
| Pancreatin | 600 milligrams |
| Lysine | 160 milligrams |
| Threonine | 100 milligrams |
| Valine | 160 milligrams |
| Leucine | 220 milligrams |
| Isoleucine | 150 milligrams |
| Arginine | 220 milligrams |
| Methionine | 500 milligrams |
| Tryptophan | 50 milligrams |
| Phenylalanine | 220 milligrams |
| Biotin | 220 micrograms |

<sup>a</sup>The Vitamin A contained a trace amount of selenium, which selenium was converted into selenium substituted fructose compounds during this example.

A first fraction was formed by mixing the Vitamin A, Vitamin E, inositol, safflower oil, liver (whole dried), sitosterol, stigmasterol, taraxasterol, cephalin, sphingomyelin, lecithin, fructose, and corn starch thoroughly together under an inert atmosphere at room temperature and pressure. A second fraction was prepared by mixing the lipoxidase, urease, and protease thoroughly together, and this second fraction was added to the first fraction and blended thoroughly therewith. Next, the antitrypsin enzyme was thoroughly mixed into the blended first and second fractions. A third fraction was prepared by mixing the Vitamin $D^3$, Vitamin $B^1$, Vitamin $B^2$, Vitamin $B^3$, Vitamin $B^4$, Vitamin $B^5$, Vitamin $B^6$, Vitamin $B^{12}$, Vitamin C, folic acid, potasium iodide, zinc sulfate, copper sulfate, choline chloride, colamine, manganese sulfate, potassium chloride, calcium phosphate (dibasic), sodium chromate (VI), stanous chloride, nickel sulfate, sodium molybdate (VI), magnesium oxide, iron II fumarate, sodium vanadate (V), para-aminobenzoic acid, citrus bioflavonoids, pancreatin, lysine, threonine, valine, leucine, isoleucine, arginine, methionine, tryptophan, phenylalanine, and biotin together. The third fraction was then thoroughly blended into the mixed first and second fractions, and the resultant mixture was heated to about 35° C. for about 1 hour and then cooled to about 20° C. for about 15 minutes. Thereafter, the mixture was again heated to a temperature of about 35° C. for about 1 hour, and then slowly cooled over a period of about 15 minutes period back to about 20° C. The resultant vitamin mixture contained various phytosterol ester vitamins, substituted fructose mineral vitamins, and diet vitamins of the present invention. This vitamin mixture was then encapsulated in 100 milligram quantities.

EXAMPLE 142

In this example, a vitamin supplement in the form of a cream was prepared in accordance with the present invention for topical administration to animals. The vitamin cream of this example was prepared in identical fashion to the vitamin pill of Example 141, with the exception that the urease, protease, antitrypsin enzyme, liver (whole dried), Vitamin $B^{12}$, folic acid, pancreatin, and iron II fumarate ingredients of Example 141 were omitted from the formulation of this example. The other ingredients set forth in Example 141 were combined in the quantities set forth in Example 141 and were reacted in accordance with the procedure given in Example 141. Moreover, in lieu of encapsulating the resultant vitamin mixture, about 1 gram of the resultant vitamin mixture was added to about 9 grams of petroleum jelly and about 90 grams of palmitic acid (reagent grade) to form a topical vitamin cream. This vitamin cream should be applied to an animal host on a daily basis.

EXAMPLE 143

In this example, a vitamin supplement in the form of a powder suitable for spraying or otherwise applying to a plant host was prepared in accordance with the present invention. The vitamin powder of this example was prepared in identical fashion to the vitamin pill of Example 141, with the exception that the liver (whole dried), antitrypsin enzyme, pancreatin, folic acid, and citrus bioflavonoids ingredients of Example 141 were omitted from the formulation of this example. The other ingredients set forth in Example 141 were combined in the quantities set forth in Example 141 and were reacted in accordance with the procedure given in Example 141. Moreover, in lieu of encapsulating the resultant vitamin mixture, about 10 grams of the resultant vitamin mixture were added to about 90 grams of ammonium sulfate (reagent grade), and thoroughly mixed therewith. This vitamin powder may be applied to the plant seeds prior to planting, turned into the soil before planting, sprayed onto the plants while growing, and/or mixed into a fertilizer which is applied to the soil surrounding the plants.

EXAMPLE 144

In this example, a vitamin supplement in the form of a liquid was prepared in accordance with the present invention for parenteral administration to animals or for spraying onto plants. The vitamin liquid of this example was prepared in identical fashion to the vitamin pill of Example 141, with the exception that the liver (whole dried), lipoxidase, urease, protease, antitrypsin enzyme, pancreatin, and citrus bioflavonoids ingredients of Example 141 were omitted from the formulation of this example. The other ingredients set forth in Example 141 were combined in the quantities set forth in Example 141 and were reacted in accordance with the procedure given in Example 141. Moreover, in lieu of encapsulating the resultant vitamin mixture, about 1 gram of the resultant vitamin mixture was then mixed with about 9 grams of safflower oil (containing about 76% linoleic acid) to form a liquid vitamin supplement.

The following example illustrates the utility of the phytosterol ester vitamin supplements, the mineral vitamin supplements, and the diet pills of the present invention.

EXAMPLE 145

In these experiments, two groups of 20 Sprague Dawley rats, 10 male and 10 female rats in each group, were used to study the effects of the diet vitamin formulations of the present invention. The starting weight for each of the rats was between about 90–135 grams. Group 1 represented the control group while group 2 was the experimental group. Both groups were fed Wayne rat chow and water ab libitum for a period of 30 days. A vitamin supplement was prepared in accordance with Example 141, but the resultant vitamin powder mixture was not encapsulated. To the Wayne rat chow fed experimental group 2 was added about 10 milligrams of the vitamin powder prepared in accordance with Example 141. Control group 1 received no vitamin supplement. Control group 1 ate 1.7% more feed during the 30 day period of the experiment than did the experimental group 2. At the end of the experiment, the animals were weighed, sacrificed, and their organs were then weighed. Table 4 below shows the results of these experiments.

TABLE 4

|  | Total Weight of Animals Before Experiment (grams) | Total Weight of Animals After Experiment (grams) | Average Percent Weight Gain Per Animal | Total Weight of Organs of Animals After Experiment (grams) | Percent of Body Weight Represented by Organs at End of Experiment |
|---|---|---|---|---|---|
| Group 1 | 2325.83 | 4882.61 | 109.93% | 335.834 | 6.9% |
| Group 2 | 2337.61 | 4837.22 | 106.93% | 340.317 | 7.0% |

From the data of Table 4, it may be seen that control group 1 gained over 3% more weight than experimental group 2 during the 30 day experimental period, even though experimental group 2 ate 1.7% more food than control group 1. These results suggest that the antitrypsin/amylase inhibitor in the vitamin supplement fed to group 2 slowed down the development of fatty tissues in that group. Moreover, the treated feed received by experimental group 2 promoted the development of the organs weighed, namely, the liver, lungs, kidneys, adrenal glands, hearts, and spleens of the animals.

The blood levels of various substances in the rats of control groups 1 and 2 were measured both before and after the experiment conducted during Example 145. For example, the levels of creatinine uric acid. glucose, and iron, were measured for both control groups 1 and 2, and the results are reported in Table 5 below.

group 2 suggests that more copper was absorbed by the animals of experimental group 2 than those of control group 1.

The concentration of blood glucose depends, at least in part, upon the activity of insulin and insulinase, as well as hexokinase in the blood. Insulin and insulinase are activated by the minerals chromium, nickel, tin and zinc, while hexokinase is activated by the mineral magnesium and further relies upon the availability of the mineral phosphorus. Decreased concentrations of glucose indicate increased activity of insulin, insulinase, and hexokinase. Hence, the lower glucose blood levels of experimental group 2 suggest that increased amounts of chromium, nickel, tin, zinc, magnesium, and phosphorous were absorbed by the animals of experimental group 2 over those of control group 1.

Finally, as shown in Table 5, the level of iron in the blood was substantially higher for the animals of experimental group 2 than those of control group 1, suggesting that significantly more iron was absorbed by the animals of experimental group 2. Additionally, since the absorption of iron into the bloodstream is dependent, at least in part, upon the availability of the mineral cobalt, these data also suggest that an increased amount of the

TABLE 5

| BLOG LEVELS OF VARIOUS SUBSTANCES DUE TO ENHANCED ABSORPTION OF MINERALS | | | | | |
|---|---|---|---|---|---|
|  | Creatinine Concentration Before Experiment | Creatinine Concentration After Experiment | Uric Acid Concentration Before Experiment | Uric Acid Concentration After Experiment | Glucose Concentration Before Experiment |
| Group 1 | 0.6 mg/100 ml | 0.5 mg/100 ml | 2.1 mg/100 ml | 1.8 mg/100 ml | 153 mg/100 ml |
| Group 2 | 0.6 mg/100 ml | 0.7 mg/100 ml | 2.1 mg/100 ml | 1.5 mg/100 ml | 153 mg/100 ml |
|  | Glucose Concentration After Experiment | Iron Concentration Before Experiment |  | Iron Concentration After Experiment |  |
| Group 1 | 151 mg/100 ml | 343 micrograms/100 ml |  | 391 micrograms/100 ml |  |
| Group 2 | 134 mg/100 ml | 343 micrograms/100 ml |  | 491 micrograms/100 ml |  |

As seen in Table 5, the concentration of creatinine increased in experimental group 2 and decreased in control group 1. An increase in blood creatinine is typically due, at least in part, to the activation of urease by the minerals molybdenum, selenium, and vanadium and the activation of arginase by the mineral manganese. Hence, the increased creatinine concentration in the blood samples of group 2 suggests that increased concentrations of molybdenum, selenium, vanadium, and manganese were absorbed by the animals of experimental group 2 over the animals in control group 1.

Further, in Table 5 above, it will be observed that the uric acid concentration in the blood of the animals of experimental group 2 decreased more than that in the animals of control group 1. Uric acid concentration is typically lowered, at least in part, through the activation of the enzyme uricase by the mineral copper. Thus, the lower uric acid concentration for experimental mineral cobalt was absorbed by the animals of experimental group 2 over those of control group 1.

During the experiment of Example 145, the rats of control groups 1 and 2 were exposed to an influenza virus. The white blood cell counts for each of control groups 1 and 2 was measured both before and after the experiment in order to determine the level of immunity of the rats exposed to the virus. Since higher white blood cell counts indicate lower immunities, and since the presence of steroids raises the immunity level, the white blood cell count is an indicator as to the steroid levels in the animals. The results of these white blood cell counts are tabulated below in Table 6.

TABLE 6

| | WHITE BLOOD CELL COUNT | |
|---|---|---|
| | Before Experiment | After Experiment |
| Group 1 | $8.9 \times 10^3$ | $11.6 \times 10^3$ |
| Group 2 | $8.9 \times 10^3$ | $9.2 \times 10^3$ |

As seen in Table 6 above, the white blood cell count for the rats of control group 1 was significantly higher than that for the rats of experimental group 2, suggesting that the steroid levels of the rats in experimental group 2 was higher than that for the rats of control group 1. This suggests that the rats of experimental group 2 absorbed significant amounts of steroids from the steroid vitamin components of the vitamin supplement administered to those rats. Moreover, it is significant to note that the rats of control group 1 became ill due to the virus while the rats of experimental group 2 remained relatively unaffected.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. A vitamin supplement which comprises a fatty acid ester of a phytosterol, the fatty acid forming said ester having from about 18 to about 20 carbon atoms in the main carbon chain.

2. A vitamin supplement as defined in claim 1 wherein the phytosterol is sitosterol.

3. A vitamin supplement as defined in claim 1 wherein the phytosterol is stigmasterol.

4. A vitamin supplement as defined in claim 1 which further comprises a pharmaceutically acceptable carrier material.

5. A vitamin supplement as defined in claim 4 wherein the phytosterol ester is in an amount sufficient to provide a daily dosage of up to about 10 milligrams of the phytosterol per kilogram of body weight.

6. A vitamin supplement as defined in claim 1 wherein the fatty acid is linoleic acid.

7. A vitamin supplement as defined in claim 1 wherein the fatty acid is linolenic acid.

8. A vitamin supplement as defined in claim 1 wherein the fatty acid is arachidonic acid.

9. A vitamin supplement as defined in claim 1 which further comprises taraxasterol.

10. A vitamin supplement as defined in claim 9 wherein said taraxasterol is combined with a second fatty acid to form an ester, said second fatty acid having from about 18 to about 20 carbon atoms in the main carbon chain.

11. A vitamin supplement as defined in claim 10 wherein said taraxasterol ester is in an amount sufficient to provide a daily dosage of up to about 2 milligrams of taraxasterol per kilogram of body weight.

12. A vitamin supplement as defined in claim 10 wherein said second fatty acid is linoleic acid.

13. A vitamin supplement as defined in claim 10 wherein said second fatty acid is linolenic acid.

14. A vitamin supplement as defined in claim 10 wherein said second fatty acid is arachidonic acid.

15. A vitamin supplement which comprises:
a fatty acid ester of sitosterol, the fatty acid forming said sitosterol ester having from about 18 to about 20 carbon atoms in the main carbon chain; and
a fatty acid ester of stigmasterol, the fatty acid forming said stigmasterol ester having from about 18 to about 20 carbon atoms in the main carbon chain.

16. A vitamin supplement as defined in claim 15 which further comprises a fatty acid ester of taraxasterol, the fatty acid forming said taraxasterol ester having from about 18 to about 20 carbon atoms in the main carbon chain.

17. A vitamin supplement as defined in claim 16 wherein the fatty acid forming said sitosterol ester, the fatty acid forming said stigmasterol ester, and the fatty acid forming said taraxasterol ester are selected from the group consisting of linoleic acid, linolenic acid, arachidonic acid, and combinations thereof.

18. A vitamin supplement as defined in claim 17 which further comprises a pharmaceutically acceptable carrier material and wherein:
the sitosterol ester is in an amount sufficient to provide a daily dosage of up to about 10 milligrams of sitosterol per kilogram of body weight;
the stigmasterol ester is in an amount sufficient to provide a daily dosage of up to about 10 milligrams of stigmasterol per kilogram of body weight; and
the taraxasterol ester is in an amount sufficient to provide a daily dosage of up to about 2 milligrams of taraxasterol per kilogram of body weight.

19. A method of achieving effective absorption of a phytosterol into a host, comprising the steps of:
condensing a fatty acid with a phytosterol to form an ester, the fatty acid having from about 18 to about 20 carbon atoms in the main carbon chain; and
administering the phytosterol ester to the host.

20. A method as defined in claim 19 wherein the phytosterol is sitosterol.

21. A method as defined in claim 19 wherein the phytosterol is stigmasterol.

22. A method as defined in claim 19 wherein the host is an animal.

23. A method as defined in claim 22 wherein the phytosterol ester is administered to the animal in an amount sufficient to provide a daily dosage of up to about 10 milligrams of sitosterol per kilogram of body weight.

24. A method as defined in claim 22 wherein the phytosterol ester is orally administered to the animal.

25. A method as defined in claim 22 wherein the phytosterol ester is topically administered to the animal.

26. A method as defined in claim 22 wherein the phytosterol ester is parenterally administered to the animal.

27. A method as defined in claim 19 wherein the host is a plant.

28. A method as defined in claim 27 wherein the phytosterol ester is administered to the plant in an amount sufficient to provide a monthly dosage of up to about 20 milligrams of the phytosterol per foot of height of the plant.

29. A method as defined in claim 19 wherein said fatty acid is linoleic acid.

30. A method as defined in claim 19 wherein said fatty acid is linolenic acid.

31. A method as defined in claim 19 wherein said fatty acid is arachidonic acid.

32. A method as defined in claim 19 further comprising the steps of:
- condensing a second fatty acid with taraxasterol to form an ester, the second fatty acid having from about 18 to about 20 carbon atoms in the main carbon chain; and
- administering the taraxasterol ester to the host.

33. A method of achieving effective absorption of sitosterol and stigmasterol into a host, comprising the steps of:
- condensing a first fatty acid with sitosterol to form an ester, the first fatty acid having from about 18 to about 20 carbon atoms in the main carbon chain;
- condensing a second fatty acid with stigmasterol to form an ester, the second fatty acid having from about 18 to about 20 carbon atoms in the main carbon chain; and
- administering the sitosterol ester and the stigmasterol ester to the host.

34. A method as defined in claim 33 further comprising the steps of:
- condensing a third fatty acid with taraxasterol to form an ester, the third fatty acid having from about 18 to about 20 carbon atoms in the main carbon chain; and
- administering the taraxasterol ester to the host.

35. A method as defined in claim 34 wherein the first, second, and third fatty acids are selected from the group consisting of linoleic acid, linolenic acid, arachidonic acid, and combinations thereof.

36. A method as defined in claim 35 wherein the host is an animal.

37. A method as defined in claim 36 wherein:
- the sitosterol ester is administered to the animal in an amount sufficient to provide a daily dosage of up to about 10 milligrams of sitosterol per kilogram of body weight;
- the stigmasterol ester is administered to the animal in an amount sufficient to provide a daily dosage of up to about 10 milligrams of stigmasterol per kilogram of body weight; and
- the taraxasterol ester is administered to the animal in an amount sufficient to provide a daily dosage of up to about 2 milligrams of taraxasterol per kilogram of body weight.

38. A method as defined in claim 37 wherein the sitosterol ester, the stigmasterol ester, and the taraxasterol ester are administered to the animal by an administration method selected from the group consisting of oral administration, topical administration, and parenteral administration.

39. A method as defined in claim 35, wherein the host is a plant.

40. A method as defined in claim 39 wherein:
- the sitosterol ester is administered to the plant in an amount sufficient to provide a monthly dosage of up to about 20 milligrams of sitosterol per foot of height of the plant;
- the stigmasterol ester is administered to the plant in an amount sufficient to provide a monthly dosage of up to about 20 milligrams of stigmasterol per foot of height of the plant; and
- the taraxasterol ester is administered to the plant in an amount sufficient to provide a monthly dosage of up to about 5 milligrams of taraxasterol per foot of height of the plant.

* * * * *

UNITED STATES PATENT AND TRADEMARK OFFICE
CERTIFICATE OF CORRECTION

PATENT NO. : 4,588,717    Page 1 of 2

DATED : May 13, 1986

INVENTOR(S) : David C. Mitchell

It is certified that error appears in the above-identified patent and that said Letters Patent is hereby corrected as shown below:

Column 5, line 12, "ensure" should be --ensuring--
Column 6, line 37, "taraxerol" should be --taraxasterol--
Column 8, line 28, "acid, bringing" should be --acid and bringing--
Column 8, line 31, "hours a" sould be --hours, a--
Column 9, line 28, "weight. produces" should be --weight, produces--
Column 10, line 19, "were" should be --was--
Column 11, line 58, "parrafin" should be --paraffin--
Column 12, line 16, "parrafin" should be --paraffin--
Column 16, line 4, "EXAMPLE 26-50" should be --EXAMPLES 26-50--
Column 17, line 58, "metabollic" sould be --metabolic--
Column 19, line 3, "invention, however" should be --invention; however--
Column 21, line 60, "witn" should be --with--
Column 23, line 47, "common, however," should be --common; however--
Column 26, line 30, "included into a pill" should be --included in a pill--

UNITED STATES PATENT AND TRADEMARK OFFICE
CERTIFICATE OF CORRECTION

PATENT NO. : 4,588,717

DATED : May 13, 1986

INVENTOR(S) : David C. Mitchell

It is certified that error appears in the above-identified patent and that said Letters Patent is hereby corrected as shown below:

Column 28, line 32, "a iron" should be --an iron--
Column 32, line 27, "a iron" should be --an iron--
Column 32, line 31, "a iron" should be --an iron--
Column 37, line 9, "then" should be --than--
Column 38, line 62, "Potasium iodide" should be --Potassium iodide--
Column 39, line 35, "potasium iodide" should be --potassium iodide--
Column 39, lines 38-39, "stanous chloride" should be --stannous chloride--
Column 39, line 50, "15 minutes period" should be --15 minutes--

Signed and Sealed this

Nineteenth Day of August 1986

[SEAL]

Attest:

DONALD J. QUIGG

Attesting Officer

Commissioner of Patents and Trademarks